(12) United States Patent
Shvets et al.

(10) Patent No.: US 8,420,014 B2
(45) Date of Patent: Apr. 16, 2013

(54) APPARATUS AND METHOD FOR MONITORING AND MEASUREMENT OF DROPLETS

(75) Inventors: Igor V. Shvets, Castleknock (IE); Cecilia Franken, Donnybrook (IE); Tomasz P. Zawada, Rathgar (IE)

(73) Assignee: Allegro Research Limited, Dublin (IE)

( * ) Notice: Subject to any disclaimer, the term of this patent is extended or adjusted under 35 U.S.C. 154(b) by 381 days.

(21) Appl. No.: 11/962,538

(22) Filed: Dec. 21, 2007

(65) Prior Publication Data
US 2008/0184809 A1    Aug. 7, 2008

(30) Foreign Application Priority Data

Dec. 21, 2006 (IE) .................................... 2006/0943

(51) Int. Cl.
*G01F 1/00* (2006.01)
(52) U.S. Cl.
USPC ....... 422/82.05; 422/400; 422/68.1; 422/501; 422/509; 422/521; 73/861; 73/1.16; 73/863.32; 73/863.71; 73/864.01; 222/71; 222/630
(58) Field of Classification Search .................... 436/43, 436/164–172; 73/861, 1.16, 863.32, 863.71, 73/864.01, 864.61; 422/68.1, 100, 103, 82.01–82.13, 422/501, 502, 400, 509, 521; 222/71, 630
See application file for complete search history.

(56) References Cited

U.S. PATENT DOCUMENTS

| | | |
|---|---|---|
| 4,328,801 A | 5/1982 | Marx et al. |
| 4,574,850 A | 3/1986 | Davis |
| 4,936,828 A | 6/1990 | Chiang |
| 5,035,150 A | 7/1991 | Tompkins |
| 5,186,057 A | 2/1993 | Everhart |
| 5,559,339 A | 9/1996 | Domanik et al. |
| 5,741,554 A | 4/1998 | Tisone |
| 5,744,099 A | 4/1998 | Chase et al. |
| 6,159,186 A | 12/2000 | Wickham et al. |
| 6,213,354 B1 | 4/2001 | Kay |
| 6,669,909 B2 | 12/2003 | Shvets et al. |
| 6,713,021 B1 * | 3/2004 | Shvets et al. .................. 422/502 |
| 6,887,431 B1 * | 5/2005 | Vann et al. .................... 422/100 |
| 7,439,072 B2 | 10/2008 | Shvets et al. |
| 2001/0050294 A1 | 12/2001 | Plattner et al. |
| 2004/0101445 A1 | 5/2004 | Shvets et al. |
| 2005/0223814 A1 * | 10/2005 | Shvets et al. .............. 73/861.08 |

FOREIGN PATENT DOCUMENTS

| | | |
|---|---|---|
| DE | 199 11 400 A1 | 9/1999 |
| EP | 1 099 484 | 6/2006 |
| WO | WO 93/09407 A | 5/1993 |
| WO | WO 2006/079926 A | 8/2006 |

OTHER PUBLICATIONS

Comley, J., "Continued Miniaturisation of Assay Technologies Drives Market for Nanolitre Dispensing," *Drug Discovery World*, Summer 2004, pp. 1-8.
Comley, J., "Nanolitre Dispensing—on the Point of Delivery," *Drug Discovery World*, Summer 2002, pp. 33-44.

(Continued)

*Primary Examiner* — In Suk Bullock
*Assistant Examiner* — Sharon Pregler
(74) *Attorney, Agent, or Firm* — Jones Day

(57) ABSTRACT

The present invention is directed to a liquid droplet monitoring and measuring apparatus for use with a liquid dispensing system of the type comprising a nozzle having a liquid dispensing tip and means for delivering the dispensed liquid through the nozzle onto a receiving substrate. Further, the invention provides a method of monitoring and measuring the volume of a liquid droplet as it is being dispensed from a liquid dispensing system comprising a nozzle having a dispensing tip. The main use for the invention is in the fields of drug discovery, genomics, medical diagnostics and other life science-related applications. The invention could also be used in other areas for example in the food industry, cosmetic industry or the chemical industry.

15 Claims, 31 Drawing Sheets

OTHER PUBLICATIONS

Rose, D., "Microdispensing Technologies in Drug Discovery," *Drug Discovery Technology*, vol. 4, issue 9, Sep. 1999, pp. 411-419.

Rose, S.D., "Applications of a Novel Microarraying System in Genomics Research and Drug Discovery," *Journal of the Association for Laboratory Automation*, vol. 3, issue 3, 1998, pp. 53-56.

Shvets et al., "Spot-on™ Technology of Low Volume Liquid Handling," *Journal of the Association for Laboratory Automation*, vol. 7, issue 6, Dec. 2002, pp. 125-129.

European Patent Office, European Search Report for related application EP 07 12 3872, dated Mar. 13, 2008.

\* cited by examiner

2. A

2. B

2. C

US 8,420,014 B2

APPARATUS AND METHOD FOR MONITORING AND MEASUREMENT OF DROPLETS

CROSS-REFERENCE TO RELATED APPLICATION

This application claims right of priority to Irish Application No. 2006/0943, filed Dec. 21, 2006, which is hereby incorporated herein by reference.

FIELD

The present invention relates to a liquid droplet monitoring and measuring apparatus for use with a liquid dispensing system of the type comprising a nozzle having a liquid dispensing tip for delivering the liquid through the nozzle onto a receiving substrate. Further, the invention provides a method of monitoring and measuring the volume of a liquid droplet as it is being dispensed from such a liquid dispensing system.

The prime field of use of the invention is in drug discovery, genomics, medical diagnostics and other life science-related applications. However, it is also contemplated that the invention may also be used in many other fields where dispensing of small droplets in the volume range of, for example, approximately 1 nanoliter to approximately 1000 microliters or even greater is required. Such fields include but are not limited to the addition of additives and flavours in perfumes, the addition of liquid ingredients during production of customised foods, the addition of liquid additives during chemical production, the manufacturing of pharmaceuticals and many other areas.

BACKGROUND

The present invention is generally related to liquid handling systems for dispensing and aspirating small volumes of liquids of the order of 1 ml and smaller, 100 microliters and smaller, or even 100 nl or smaller. Liquid handling systems are being provided and will be provided in the future for the dispensation of droplets of even smaller volumes.

The present invention is particularly directed to liquid handling systems used in life science, medical and pharmaceutical sectors for applications such as high throughput screening, microarraying, Polymerase Chain Reaction (PCR), combinatorial chemistry, proteomics, protein crystallography, genetic screening and others. The invention may also be used for medical diagnostics e.g. for printing reagents on a substrate covered with bodily fluids or for printing bodily fluids on substrates.

The development of instrumentation for dispensing minute volumes of liquids has been an important area of technological progress for some time. Numerous devices for dispensing of small volumes of liquids of the order of 100 microliters and smaller have been developed over the past twenty-five years.

The requirements of a dispensing system vary significantly depending on the application. For example the main requirement of a dispensing system for ink jet applications is to deliver a droplet of a fixed volume with a high repetition rate. The separation between individual nozzles making up the ink jet dispenser should be as small as possible so that a number of nozzles may be accommodated on a single printing cartridge. For this particular end use, the task is simplified by the fact that the properties of the liquid dispensed, namely ink, are well defined and consistent.

On the contrary, for life science, medical and pharmaceutical applications the requirements are completely different. The system should be capable of handling a variety of liquids with different mechanical and physical properties, e.g. viscosity. For many such applications it is important to be able to freely adjust the volume dispensed. Recent inventions related to the field of small volume liquid handling are covered by numerous patent applications, e.g. U.S. Pat. No. 5,744,099 (Chase et al); U.S. Pat. No. 4,574,850 (Davis); U.S. Pat. No. 5,035,150 (Tomkins), U.S. Pat. No. 5,741,554 (Tisone); U.S. Pat. No. 6,713,021 (Shvets), U.S. Pat. No. 6,669,909 (Shvets) and are also described in the following scientific and technical publications:

J. Comley, Nanoliter Dispensing—on the Point of Delivery, Drug Discovery World, Summer 2002, p 33-44;

D. Rose, Microdispensing Technologies in Drug Discovery, Drug Discovery Technology, vol 4, N9, September 1999, p 411-419;

S. D. Rose, Applications of a Novel Microarraying System in Genomics Research and Drug Discovery, Journal of the Association for Laboratory Automation, vol 3, N3, 1998, p 53-56;

I. V. Shvets, S. Makarov, C. Franken, A. Shvets, D. Sweney, J. Osing, Spot on Technology of low volume liquid handling, Journal of Association of Laboratory Automation, vol 7, N 6, December 2002, p 127-131.

The wide variety of the mechanical properties of liquids and the very nature of many biological liquids often make consistent dispensing difficult. For example the dispenser can be easily blocked by a clot as these are readily formed in cell-based liquids and protein solutions. Therefore, it is highly desirable to be able to verify that the instrument is dispensing correctly and in many cases to be able to detect the moment when the dispenser runs out of the liquid or starts malfunctioning. It is also desirable to be able to detect if the liquid handling instrument leaks or if a drop fails to separate from the dispensing nozzle of the instrument. Additionally, in many instances, it is advantageous to be able to measure the volume of the droplet dispensed to ensure that it does correspond to the amount requested by the operator of the dispensing system. Independent verification of the volume dispensed becomes more and more important as the users have to operate in an environment of increasing legal regulation. For example, failure to dispense a drop may lead to an incorrect result of a medical test and consequently to incorrect diagnosis. Therefore, the user requirement for availability of such measurement technologies for operation verification intensifies.

It is also desirable for manufacturers of various liquid handling instruments to have in-house instrument test and calibration tools. During the production phase and also during the phase of development of new liquid handling instruments, it is important to have tools for quality control, calibration, tuning and optimisation of the instruments.

The issue of droplet volume measurement for small volume dispensing is also important from a psychological perspective. The reason is that in many cases the operator cannot readily monitor visually arrival of a tiny drop to a destination substrate, in particular, if the destination substrate is not flat. This adds to the user discomfort even if the dispenser functions properly as the user cannot readily satisfy this by simple visual monitoring.

It is difficult to fulfil challenging requirements for a successful system for measurement of droplet volume during dispensing. For many applications the ideal system must measure the volume in non-contact mode meaning that direct transfer of the drop to a measurement device, such as microbalance, is not an option.

U.S. Pat. No. 5,559,339 (Domanik) teaches a method for verifying a dispensing of a liquid droplet of relatively large size from a nozzle. The method is based on coupling of light from a source to a receiver. As a droplet of liquid travels from the nozzle it obstructs the coupling and therefore, the intensity of the signal detected by the receiver is reduced. The disadvantage of this method is that it is based on the absorption of electromagnetic radiation (in practice light) by the droplet. For a range of applications where minute droplets of liquids with a broad range of optical properties need to be dispensed may present a challenge. Another limitation of U.S. Pat. No. 5,559,339 (Domanik) is that for many applications it is desirable not only to confirm that a droplet has been dispensed but also extract information on the size of the droplet, and its velocity and shape. U.S. Pat. No. 5,559,339 did not focus on these issues.

There are many inventions dealing with the control of the dispensing for the ink jet printing applications. It should be noted that in the ink jet printing application the range of the droplet volumes is entirely different to the range of interest in the present application. In ink jet printing application the droplets often have the volume in the pico-liter range. This is some 100 times smaller than the typical droplets dealt with in the present invention which are normally in the range from 10 nl to 50-1000 microliters. Therefore many approaches developed for the applications in ink jet printing are not suitable for the field of dispensing for life science and drug discovery.

Furthermore, many inventions in the ink-jet field are directed to monitoring the passage of the droplet amounts to simple observation of the signal intensity reduction on the detector or measuring time lag between two signals from the two adjacent detectors. These inventions usually do not teach how more complex analysis of the droplet could be obtained from the measurements.

There is another substantial difference between the inventions related to the ink jet printing and the one from the field of use of the present invention. For droplets as small as used in ink jet printing, the volume of the droplet is related to its size via a simple relationship: the volume is proportional to the third power of its size. This is merely a reflection of the fact that the droplet has a sphere-like shape. The greater is the size of the droplet, the greater is the absorption of light passing through it. This simple relationship is the basis of the volume measurements methods in some of the above patents. In contrast, as it will be clear from the description below, in the droplet volume range that is of interest for the field of use of the present invention (for example, 1000 µl or less, preferably 1 nl to 1000 µl, 10 nl to 100 µl, and/or 5 nl to 50 µl), this relationship generally is not valid. Therefore, the methods described for other applications (ink-jet, etc.) could not be applied in the present invention.

For measurement of the droplet volume for the field of use of the present invention, i.e. low volume liquid handling for life science and medical fields, the most common method used is based on electric measurements. The detection relies on measurements of a charge carried by a droplet. The droplets are typically charged by applying a high voltage to the dispenser. The charge carried by the droplet is reflective of the droplet's size. In some inventions it is proposed using a Faraday pail for this purpose (U.S. Pat. No. 6,713,021 (Shvets); European Patent No 1,099,484 (Shvets); U.S. Pat. No. 6,669,909 (Shvets)). Faraday pails are well known and described in many published documents. Essentially the Faraday pail consists of an inner box and a shield. The shield and the box are well insulated from each other. In this situation a charged droplet arriving at the box induces a charge of the opposite sign and same magnitude at the surface of the box. This charge is created by the current flowing to the inner box and it can be measured by a charge measurement circuit. Generally the dispenser and hence the nozzle are maintained at a relatively high voltage. The shield and box are connected to ground potential. The charge can also be measured without catching the droplet in the pail. For this the pail is made in the shape of a cylinder without a bottom. Thus, the charged droplets progress through the Faraday pail that serves as an induced charge detector. The Faraday pail can be used to detect the moment when the droplet enters into the box and leaves it. Therefore, it can be used to measure the droplet's velocity, as the length of the box is known.

The Faraday pail has a number of disadvantages. One of the disadvantages is that it is sensitive to external electromagnetic noise, e.g. noise at 50 or 60 Hz frequency. To measure the volumes of small drops, the sensitivity of the Faraday pail must be optimised meaning that the entry and exit holes of the shield and the inner box must be reduced in size. This increases the chances of missing the exit hole and thus leaving the drop attached to the wall of the inner chamber. Another disadvantage is that in order to increase the charge carried by the droplet and thus improve the sensitivity of the instrument, it is often necessary to apply as high a voltage to the dispenser as possible. This may create further complications; e.g. the risk of destroying a charge sensitive amplifier connected to the pail, the risk of the malfunctioning of high voltage equipment with consequent danger for the operator, etc.

U.S. patent application Ser. No. 10/787,229 filed Feb. 27, 2004 (Shvets et al) describes alternative method of droplet volume detection based on changing the capacitance of the sensor positioned around the nozzle. According to the method, the capacitance between the sensor and the nozzle is measured. Once the droplet is ejected from the nozzle, it increases the capacitance for a short period of time. The volume of the liquid dispensed can be determined from the shape of the electric signal induced in the sensor related to its capacitance change.

The key problem with the many of the droplet volume measurement inventions for the field of low volume liquid handling in life science is the low conductivity of many relevant liquids. Unlike in the case of the ink jet printing where the formulation of the ink could be modified to suit the requirements of the printer, in the area of life sciences it is often not possible to change the formulation of the liquid. Therefore, there is no simple way to increase its conductivity.

U.S. Pat. No. 6,669,909 (Shvets) also describes another method for droplet detection that is very specific to the dispensing apparatus. It is related to monitoring the force acting on the actuator in the dispensing apparatus and also the displacement of the actuator. Unfortunately, this method can only be used with a specific type of the dispensing apparatus.

To summarise, at present the issue of reliable detection and measurement of the volume of droplets dispensed for applications in life science, medical diagnostics, drug discovery and pharmaceutical areas is still not fully resolved. It is suggested that the lack of a commonly acceptable measurement technology impedes wider use of low-volume liquid handling equipment. The same applies to the low volume liquid dispensing for certain other applications outside the field of life science.

SUMMARY

The present invention relates to providing methods and apparatuses for the monitoring and/or measurement of the dispensing of volumes of liquids dispensed in the ranges of approximately 1 nl to 1000 µl, preferably 1 nl to 100 µl, more preferably 5 nl to 50 µl.

The volume of a drop may be measured as it travels from the dispenser to a destination location, in a non-contact mode, i.e. so that the liquid jet/droplet does not come in contact with the measuring device. The timing of the start of dispensing and the end of dispensing may be detected. A single dispensing event may be verified, as may be the absence of leakage from the dispenser or blockage of the dispenser.

The methods and apparatuses may allow for monitoring whether or not the liquid is left at the end of the dispensing tip of the nozzle of the dispenser after the dispensation, i.e. monitoring if a hanging drop develops at the dispenser, and detection of the moment when the dispenser runs out of liquid.

The methods and apparatuses may also allow for the monitoring of the velocity of the jet ejected by the dispenser, establishing the position of the nozzle, and/or confirmation of arrival of the nozzle of dispenser to the dispensing position.

STATEMENTS OF THE INVENTION

According to a first aspect of the invention, there is provided a method for monitoring and measuring the volume of liquid dispensed in a single dispensing event from a liquid dispensing system comprising the steps of monitoring and measuring the volume of a dispensed liquid jet while the dispensed liquid maintains a cylindrical or quasi-cylindrical shape.

The invention is suitable for monitoring and measuring a liquid droplet volume of less than approximately 1000 µl but greater than 1 nl. Preferably, the volume of the dispensed liquid jet is from approximately 1 nl to approximately 1000 µl, more preferably from 5 nl to 50 µl. As outlined in the Background section above, this is an important advantage of the present invention.

Furthermore, the present invention has advantageously recognized that droplets dispensed in this size range have different characteristics to droplets outside this general size range. For example, ink used in ink jet printing when dispensed will form a sphere-like shape and its volume can be calculated by the simple relationship between the volume and size. This is expanded on above. However, this simple relationship is not true of liquid droplets dispensed according to the present invention and this is expanded on in detail in the Detailed Description below. The present invention advantageously addresses this aspect.

It will be understood that the present invention is concerned with monitoring and measuring a liquid jet as it is dispensed when the jet is in the form of a cylindrical jet or quasi-cylindrical jet, or anywhere in between these two forms. Furthermore, for the purposes of this invention, the term "quasi-cylindrical" will be understood to also encompass the liquid jet when it is in the form of a series of sub-droplets which are of the same size with equal separation between the droplets, immediately prior to the formation of distinct spherical droplets or sub-droplets from the dispensed jet. Thus, the "quasi-cylindrical jet" according to the present invention, encompasses the liquid jet before it becomes one or more droplets (FIG. 2c).

It is also important to note that the term "quasi-cylindrical" covers both liquids dispensed from circular and/or non-circular nozzles. For example, a nozzle may have opening of any cross-section, including circular, square, rectangular or oval cross-sections. As capillaries of circular cross-section are readily available from numerous manufacturers of capillaries, these are generally used in practice. It will be understood that even if a jet is ejected from a non-circular nozzle, it will evolve to the circular cross-section due to the action of surface tension as it travels away from the nozzle. This will normally happen after several oscillations of the cross-sectional shape taking place as the jet travels away from the nozzle.

According to one embodiment of the invention, the method is carried out as the liquid jet is discharged from the liquid dispensing system.

Ideally, the cylindrical or quasi-cylindrical volume of a dispensed liquid jet is monitored and/or measured before the dispensed liquid jet becomes one or more distinct droplets, such as distinct spherical droplets. Thus, the liquid jet may be monitored as a series of sub-droplets.

Ideally, the method comprises providing an optical sensing unit at a distance from the liquid dispensing tip such that the liquid jet is sensed substantially as a cylindrical or quasi-cylindrical jet segment dispensed from the tip, and measuring the change in optical signal output from the optical sensing unit to determine the volume of the liquid jet.

It will be understood that the liquid to be dispensed can be any liquid, ideally for use in the life sciences field, medical diagnostics and drug development.

Advantageously, the present invention addresses one of the main problems associated with droplet volume measurement of low volume liquid for the life sciences field. Known techniques use conductivity to measure volume, however, most liquids used in the life sciences field have low conductivity which cannot be modified for use with known systems. The present invention provides an alternative solution for volume measurement of this type of liquid. Furthermore, the type of liquid dispensed according to the invention have different characteristics (in terms of transparency for example) to, for example, ink for ink jet printing. The present invention also addresses these issues.

Ideally, the liquid dispensing system comprises a nozzle having a liquid dispensing tip and means for delivering the liquid through the nozzle onto a receiving substrate. Other liquid dispensing systems may be contemplated for use with the present invention.

Another major advantage of the present invention is that it is a non-contact method, thus, no problems of contamination of the liquid being measured will arise. This is a great benefit when dealing with sensitive biological samples for medical or other uses.

According to one embodiment of the invention the optical sensing unit is placed adjacent to the nozzle dispensing tip as the liquid jet is being discharged from the nozzle. Thus, the dispensed liquid jet alters the optical coupling between an optical source unit and an optical detector unit. Various measurements can be taken including the following:

The time taken for the cylindrical or quasi-cylindrical liquid jet to pass through the sensing area of the optical sensing unit can be measured.

Furthermore, the volume of the dispensed liquid jet can be determined by measuring and calculating the following parameters:

a. the time ($t_j$) required for the cylindrical or quasi-cylindrical liquid jet to pass in front or through the sensing area of the optical sensing unit;
b. the liquid droplet velocity is calculated from the timing of the rising and/or falling fronts of the signal detected by the optical sensing unit;
c. the liquid droplet length is calculated based on the liquid droplet velocity and the time $t_j$, and
d. the mean cross-sectional area of the cylindrical or quasi-cylindrical jet is obtained from i. one or more separate calibration measurements; or ii. with reference to the cross-sectional area of the nozzle.

According to a preferred embodiment of the invention, the method comprises the steps of carrying out the dispensing event two or more times wherein the separation distance between the liquid dispensing nozzle and the optical sensing unit for each separate event differs and the liquid jet velocity is calculated from the time difference in the optical signals resulting from these separate dispensing events.

According to another embodiment of the invention, the velocity of the liquid jet is calculated from the known separation distance between the optical sensing unit and the nozzle using time delay between the start of a dispensing event and the detection of the liquid jet by the optical sensing unit.

According to yet another embodiment of the invention, the optical signal output is measured as the liquid is discharged from the nozzle dispensing tip whereby the volume of liquid dispensed and the termination of the discharge may be monitored and recorded.

Optionally, an initial calibration step may be performed and the optical signal data is saved for subsequent use.

A further embodiment of the invention provides a method for monitoring and measuring the volume of a dispensed liquid jet, preferably from approximately 10 nl to approximately 10 µl in volume, as it is being discharged from a liquid dispensing system, the method comprising providing an optical sensing unit at a distance from a liquid dispensing nozzle such that the liquid jet is sensed as sphere-like shape, measuring the change in signal output from the optical sensing unit, and calculating the liquid jet volume according to the following formula:

$$vol = K \cdot \int s(t) dt$$

where s(t) is an output signal and K is scaling factor.

According to a second aspect of the invention, there is provided a liquid droplet monitoring and measuring apparatus for measuring the volume of a dispensed liquid jet as it is being discharged from a liquid dispensing system, the apparatus comprising an optical sensing unit located at a distance, preferably a set distance, from a liquid dispensing tip such that the liquid jet is sensed as a cylindrical or quasi-cylindrical jet dispensed from the tip, and a means for measuring the change in optical signal output from the optical sensing unit as the liquid jet is being dispensed.

Ideally, the dispensed liquid jet volume is from approximately 1, 10 or 100 nanoliters to approximately 1000 µl. Volumes greater than 1000 µl may also be contemplated.

Generally, the liquid dispensing system comprises a nozzle having a liquid dispensing tip and means for delivering the liquid through the nozzle onto a receiving substrate, According to a preferred embodiment of the invention, the optical sensing unit has an optical housing unit having a body, one or more optical fibres, a means for accommodating the one or more optical fibres which are connectable with one or more optical (e.g. light) sources, one or more optical (e.g. light) detectors and a means for mounting the optical housing unit adjacent to the dispensing tip.

According to a more preferred embodiment, the optical housing unit comprises an optical housing body;

at least two optical fibres located adjacent to a liquid dispensing tip;

at least one optical (e.g. light) source coupled to the optical fibres; and at least one optical (e.g. light) detector.

Ideally, the optical housing unit comprises one or more pairs of optical fibres, preferably two pairs of optical fibres.

Alternatively, the apparatus comprises one pair of optical fibres, one optical (light) source and one optical (e.g. light) detector.

According to another embodiment of the invention, the angle between the pair of optical fibres one of which is connected to the light source and the other one connected to the detector is from 45° to 180°, preferably 90°.

Ideally, the optical fibres are releasably or permanently fixed to the optical housing body.

According to one embodiment of the invention, the open ends of the optical fibres are located substantially parallel to the path of the dispensed liquid jet.

According to another embodiment, the optical fibres are located at an angle with the path of the dispersed liquid jet.

According to yet another embodiment, the distance from the optical fibres to the path of the dispensed liquid droplet is from approximately 0.1 to approximately 20 mm.

According to still another embodiment the distance between each optical fibre and the path of the dispersed liquid droplet is different.

The optical source unit (e.g. light source) may be a LED or a diode laser. The detector may be a phase sensitive detector, preferably equipped with a PIN diode or a photodiode.

According to a third aspect of the present invention, there is provided a method for monitoring and measuring the volume of liquid dispensed from a liquid dispensing system in the volume range from 1 nl to 1000 µl, preferably from 10 nl to 100 µl more preferably from 5 nl to 50 µl in which the liquid jet alters the optical coupling between an optical source and optical detector.

This aspect also provides that when liquid is not being intentionally discharged from the liquid dispensing system the optical signal is monitored in order to provide an indication of a possible malfunction in the system. This allows the monitoring of leaks from the liquid dispensing system which may not necessarily from a cylindrical or quasi-cylindrical jet shape.

According to a fourth aspect of the present invention, there is provided a dispensing assembly for liquid droplets of the order of approximately 1000 µl or less in volume, preferably from 1 nl to 1000 µl, more preferably from approximately 10 nanoliters to approximately 10 µl, even more preferably from 5 nl to 50 µl, of the type comprising a nozzle having a liquid dispensing tip and means for delivering the liquid through the nozzle onto a receiving substrate, wherein the assembly further comprises the liquid droplet monitoring and measuring apparatus as defined above.

The invention will now be more clearly understood from the following description of some embodiments thereof given by way of example only with reference to the accompanying drawings.

DETAILED DESCRIPTION

It is important to note that droplets ejected from nozzles do not necessarily have a sphere-like shape. The shape of a droplet depends on the volume of the droplet, its velocity and the distance from the nozzle to the point where the shape is examined. The shape of the droplet changes as the droplet travels between the nozzle and the destination substrate. For example, a 200 nl volume ejected from a nozzle with the diameter of 0.152 mm turns into an approximately 11 mm long jet segment. Likewise, the 2 μl droplet ejected from the same nozzle forms an approximately 110 mm long segment. It should be stressed that the diameter of the jet does not necessarily equal the inner diameter of the nozzle. Very often the diameter of the jet is somewhere in between of the inner and outer diameters of the nozzle. For example in the case of experiments described in this specification, a jet ejected from the nozzle with diameter of 0.152 mm had a diameter of approximately 0.180 mm. The jet diameter depends on the jet velocity and generally the higher the jet velocity, the closer the diameter of the jet is to the inner diameter of the nozzle. As the jet segment travels though the air, it breaks into several sub-segments and then, with longer travel the sub-segments form the sphere-like droplets. This happens under the influence of the surface tension that favours the spherical shape over the cylindrical one. If the droplets travel through the air faster, their shape deviation from the sphere will be greater, due to the mechanical resistance of air to their travel. This consideration is in stark contrast with the situations in inventions relating to ink jet printing where the droplet is almost invariably considered to be sphere-like. The reason for this difference is substantially different volume of the droplet. The volumes of ejections for ink jet printing are typically well below 100 nl and even below 1 nl. Therefore, these droplets turn into the spherical-like objects much faster than the typical droplets used in the field of the present invention.

Figure 1:
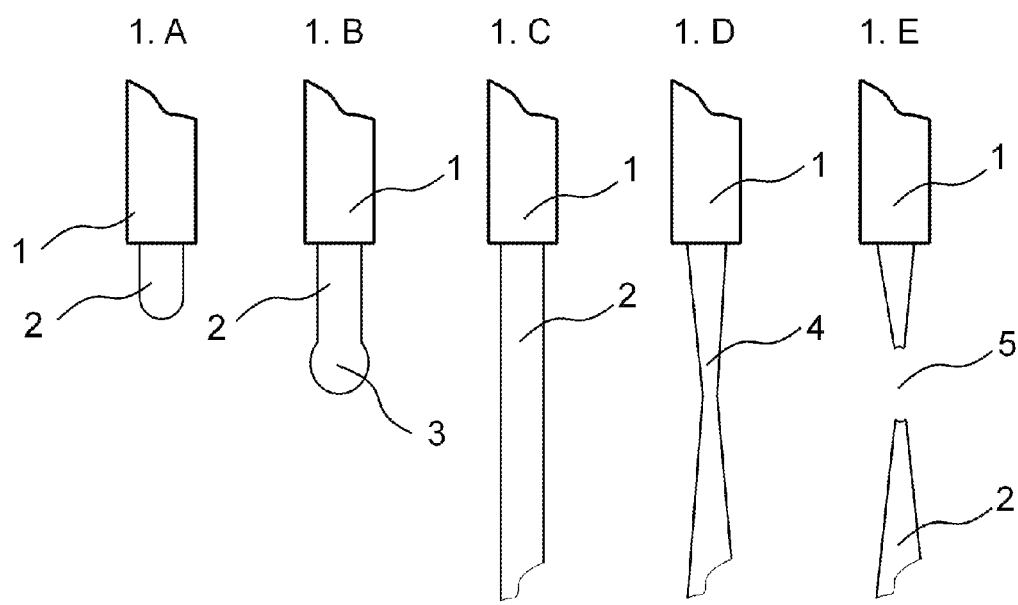
FIG. 1 is a schematic illustration of the initial stages of development of a droplet over the time and evolution of its shape.

FIG. 1 shows the initial stages of the droplet formulation process. FIG. 1A shows the initial stage of a droplet emerging from a nozzle tip 1 which can be modelled as cylinder of liquid 2 emerging from the nozzle tip 1. This is shown in FIG. 1A. FIG. 1B then shows the frontal end of the cylinder 2 forming a sphere-like shape 3. FIG. 1C shows the cylinder of liquid as it continues to exit from the nozzle tip 2. The sphere-like shape at the end of the cylinder is not shown in this diagrammatic representation. Once the nozzle is closed, a constriction 4 develops along the cylinder in the vicinity of the nozzle tip 1 (FIG. 1D). The constriction 4 breaks up at the location indicated by the numeral 5 and the jet is separated from the nozzle (FIG. 1E).

Figure 2:
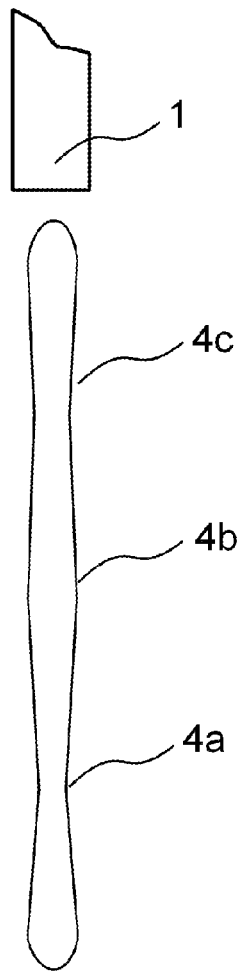
FIG. 2 is a schematic illustration of the later stages of the evolution of the droplet's shape.
Figure 2:
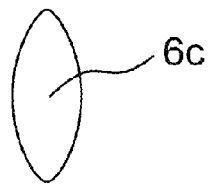
Figure 2:
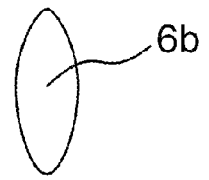
Figure 2:
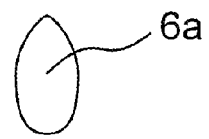
Figure 2:
Figure 2:
Figure 2:

The evolution of the jet as it travels away from the nozzle is schematically indicated in FIG. 2. Multiple constrictions develop along the jet as shown in FIG. 2A. These constrictions are indicated by the numerals $4a$, $4c$. FIG. 2A shows the case of two constrictions being developed. The constrictions represent instability in the continuous jet. The fastest growing mode of instability has the wavelength of approximately $\lambda = 9R_o$ where the $R_o$ is the radius of the jet. Here number 9 is an approximation resulting from analytical models. These constrictions separate the jet into the droplets indicated by the numerals $6a$, $6b$, $6c$, etc having the separation between the consecutive droplets of approximately $9R_o$. The time $t_{breakup}$ required to separate the jet into the droplets is calculated according to the formula $t_{breakup} = k(\rho R_o^3/\sigma)^{1/2}$, where σ is the surface tension of the liquid and ρ is density, k is a numerical constant that depending on the model used is in the range of 1 to 3. This formula is suitable for liquids of low viscosity μ. For liquids of high viscosity other formulas need to be used to describe $t_{breakup}$. The droplets will not immediately acquire the spherical shape. Instead they will gradually become more spherical by expanding their cross-section in the plane orthogonal to the travel direction and reducing their length along the travel direction. The droplets oscillate and change from the elongated spheroids as shown in FIG. 2B by the numerals $6a$, $6b$, $6c$ to the contracted spheroids as shown in FIG. 2C and vice versa. After a number of oscillations they will settle to a sphere-like shape and then continue maintaining this shape until they reach the destination substrate provided it is located close enough. If the destination substrate is located far away, then the evolution of the jet will continue further, the separations between the spherical drops will change and some of them may collide and others may start moving in directions away from the overall jet trajectory. This further evolution of the jet is not shown in FIG. 2.

To summarise, the dynamics of the shape evolution of the droplets is defined by the droplet volume, velocity, surface tension of the liquid σ, its viscosity μ, its density ρ, diameter of the nozzle and other factors. Therefore the dynamics of droplet formation differs significantly between the field of use of the present invention, i.e. liquid handling for the medical diagnostics, drug discovery, life science research and droplet formation in ink jet printing.

The present invention is directed to the specific pathway of the droplet shape evolution related to the specific field of use. This is characterised generally by the volume of the liquid dispensed of 20 nm or greater and the diameter of the nozzle of 80 micrometer or greater, the droplet velocity of in the range of 0.1 µm/s to 50 m/s. Furthermore, the present invention is directed to a range of typical liquids used in medical diagnostics, pharmaceutical applications, life science research, genomics, proteomics and drug discovery process.

Figure 3:
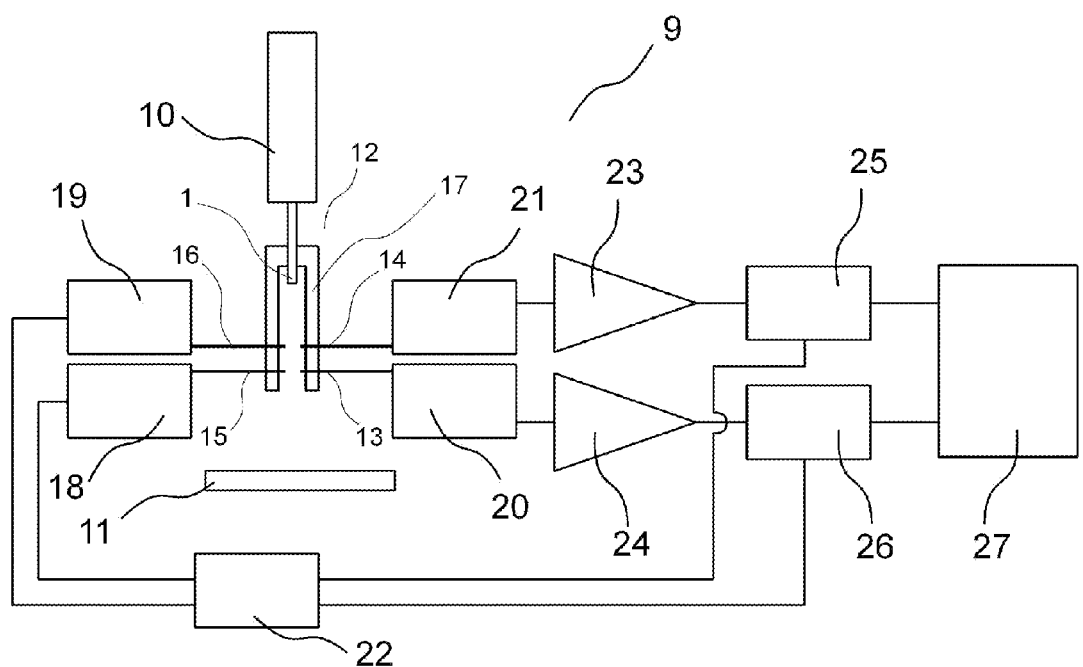
FIG. 3 shows the schematics of the instrument for measurements of the droplet volume according to the present invention.

FIG. 3 shows a schematic diagram of the instrument 9 for measurements of the droplet volume according to one embodiment of the present invention. The dispensing device is shown by reference numeral 10. In the experiments described herein the dispensing device as described in the U.S. Pat. No. 6,713,021 (Shvets) and U.S. Pat. No. 6,669,909 (Shvets) may be used. This device is based on the proprietary SpotOn™ technology. The device is capable of dispensing a variety of liquids with different mechanical and optical properties in the volume range from 20 nl to well over 100 microliters. The nozzle 1 of the dispensing tip is circular and has cross-section of 0.152 mm. The invention is not limited to this specific type of dispensing device or dispensing technology. For example, the dispensers utilizing a solenoid valve or micro-solenoid valve is another possible choice of dispensing device for use with the present invention. Another suitable example of dispensing device is an instrument utilizing automated syringes.

As shown in FIG. 3 the dispensing device delivers droplet to a destination substrate 11. The destination substrate could be a microtiter plate or well plate or any other substrate or surface. An optical housing unit 12 is positioned in the vicinity of the nozzle 1. The optical housing 12 unit is described in greater detail in FIGS. 4 and 5.

Figure 4:
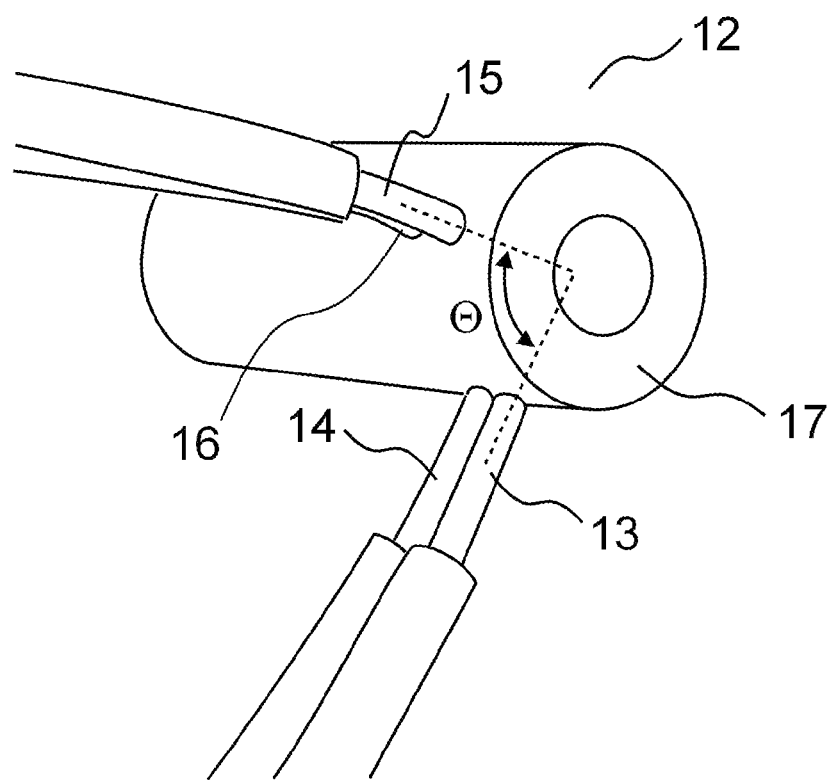
FIG. 4 shows the schematics of the optical housing unit according to the present invention.
Figure 5:
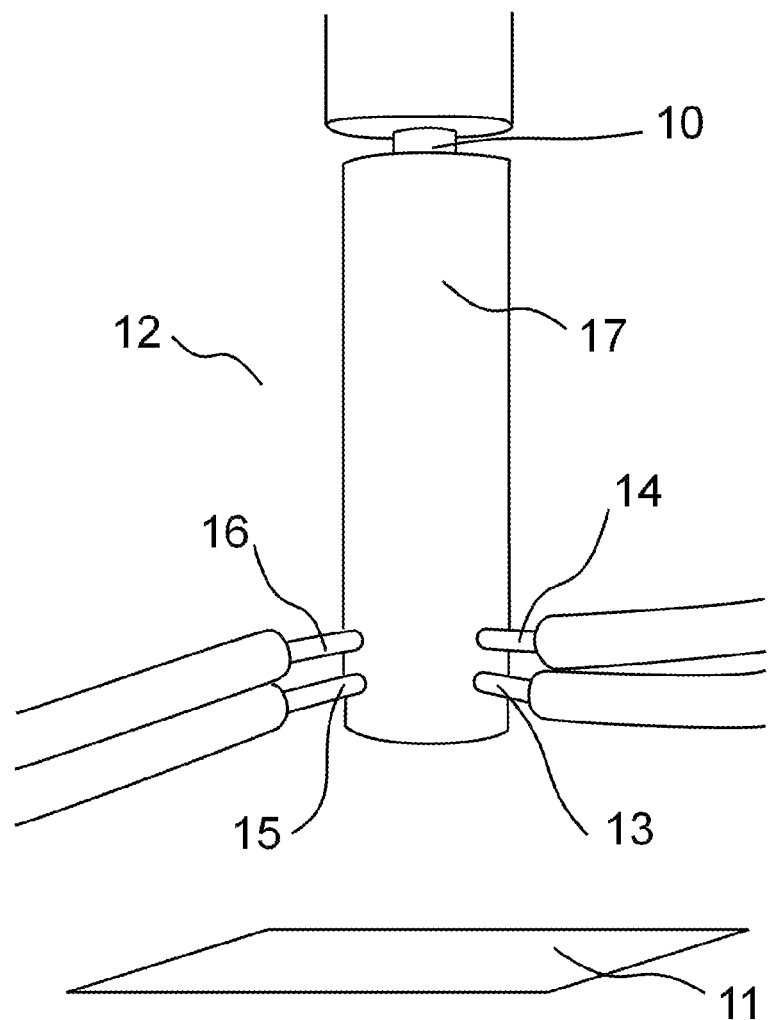
FIG. 5 shows the schematics of the optical housing unit from a different viewpoint according to the present invention.

The optical housing unit 12 shown in FIGS. 4 and 5 is capable of accommodating two pairs of optical fibers. Embodiments could be readily devices that accommodate three, four, five, six or indeed greater number of fibers. As it will be clear from the description below in some embodiments the optical housing unit may also accommodate just one pair of optical fibers, e.g. fibers 13 and 15. The optical fibers coupled into the unit are indicated by numerals 13, 14, 15, 16. In the embodiment described herein optical fibers have core diameter of 1 mm and outer jacket of 2.2 mm. Optical fibers with other core and jacket diameter values could be used as well. The optical fibers are fixed in the body 17 of the optical hosing unit either by means of adhesive or by other suitable means, e.g. tight fit. The angle between the fibers 13 and 15 is Θ. This angle could be equal to the angle between the fibers 14 and 16 or alternatively in other embodiments it could also be different. For simplicity of FIG. 4 we will refer to the case when the fibers 13 and 14 enter into the body 17 of the optical housing unit parallel to each other as well as the optical fibers 15 and 16. Moreover, for simplicity we assume that all the fibers 13, 14, 15, 16 are orthogonal to the axis of the body 17 of the housing unit. This is more clearly shown in FIG. 5 picturing the optical housing unit 12 from a different viewpoint. It should be appreciated that both pairs of optical fibers 13 and 14 and optical fibers 15 and 16 do not have to be parallel to each other. It should be appreciated that they do not have to enter into the body 17 of the optical housing unit 12 in the direction orthogonal to its axis. In a typical embodiment the separation between the end of the fibers 13, 14, 15, 16 and line of the path of the droplet is in the range of 0.1 to 10 mm. This separation is optimized experimentally and it depends on the type of the fibers used and their numerical aperture. Furthermore, the separation between the path of the jet and the end of the fiber 13 does not have to be equal to the same for the fiber 15. The same applies to the fibers 14 and 16.

Figure 6A:
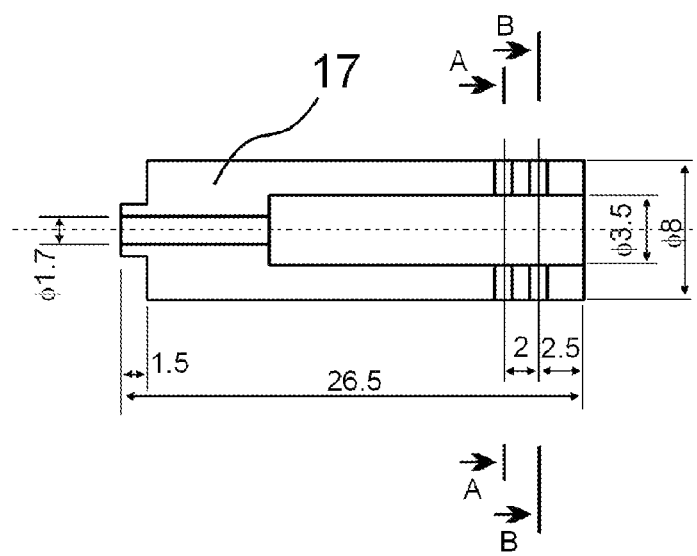
FIG. 6 shows an axial and radial cross-section of the body of the optical housing unit used in an embodiment described in the present specification.
Figure 6B:
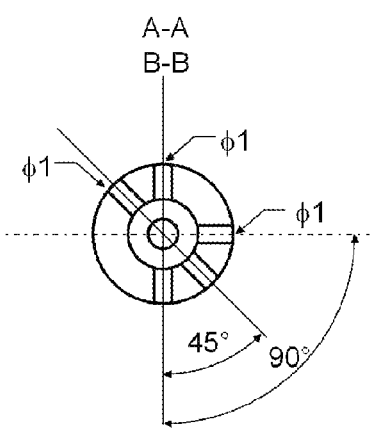

In a typical embodiment the path of the droplet in the optical housing unit 12 coincides with the axis of the unit but this may not be the case in all embodiments. In addition, the device may have an optical housing unit with an asymmetric body 17. The body 17 of the optical housing unit may be made of plastic, metal or another suitable material. The body 17 of the housing unit 12 is made in such a way that the droplets preferably travel in front of the ends/terminations of the optical fibers 13, 14, 15, 16. Furthermore, in the embodiment described herein, the angle Θ between the fibers 13 and 15 and the fibers 14 and 16 could be altered. This is shown by cross-sections through the body of the optical housing unit 12 (FIGS. 6A and 6B).

In this specification we describe the experiments carried out with the angle Θ of 45°, 90°, 135°, 180°. The optical fibers in this embodiment are located in such a way that the fibers 14 and 16 are located at the same distance away from the nozzle 1. Likewise, the fibers 13 and 15 are located at the same distance away from the nozzle 1. Other embodiments of this device may be contemplated. The separation between the optical fibers 13 and 14 and the fibers 15 and 15 is 2 mm as shown in FIG. 6. Again, embodiments with other separations could be contemplated. In the embodiment described here the separation between the ends of the fibers 14 and 16 and the nozzle 1 is 0.3 mm.

Returning to FIG. 3, optical fibers 15 and 16 are coupled into light sources 18 and 19. In the embodiment described herein, two light-emitting diodes LED SFH756V are employed as the light sources 18 and 19. Thus, the dominant radiation light wavelength is 660 nm. Therefore, the light from the light source can be delivered into the optical fibers 15 and 16 and then towards the ends of the fibers facing the droplet's path. The optical fibers 13 and 14 are coupled into detectors 20 and 21. In the embodiment described in this specification SFH250V PIN diode were employed as detectors 20 and 21. This selected diode is sensitive to the light at approximately 660 nm wavelength. Both selected devices, the LED and the PIN diode, are suitable for work with fiber and have packaging convenient for coupling to the fiber.

Reference numeral 22 indicates the phase and frequency modulation unit. This is the unit capable of generating two signals at frequencies $f_1$ and $f_2$ and another two signals with the same frequencies $f_1$ and $f_2$ but phases offset by the desired phase shifts: $\phi_{0.1}$ and $\phi_{0.2}$.

In the embodiment described herein the phase and frequency modulation unit employed digital phase controller utilizing the advanced event module build-in the TMS320F2812 DSP microcontroller. It will be understood that other devices could be employed to construct the phase and frequency modulation unit 22, for example it could be based on analogue circuits. The settings of the TMS320F2812 DSP microcontroller are controlled by RS232 interface. The resolution of frequency setting is 1 Hz and 1° for phase. Reference numerals 23 and 24 are amplifiers and 25 and 26 indicate phase-sensitive detectors, known also as lock-in amplifiers. The phase and frequency modulation unit 22 modulates the light emitted by the light sources 18 and 19 as shown schematically in FIG. 3. This is done by means of supplying the modulation signals at the frequencies $f_1$ and $f_2$ to the light sources 18 and 19. The unit 22 also supplies the reference signal to the phase-sensitive detectors 25 and 26.

Therefore, the remaining two signals produced by the modulation unit 22 shifted by phases $\phi_1$ and $\phi_{0.2}$ are supplied to the phase-sensitive detectors 25 and 26. The signal from the phase sensitive detector 25 and 26 is supplied to the signal processing unit 27.

Figure 7:
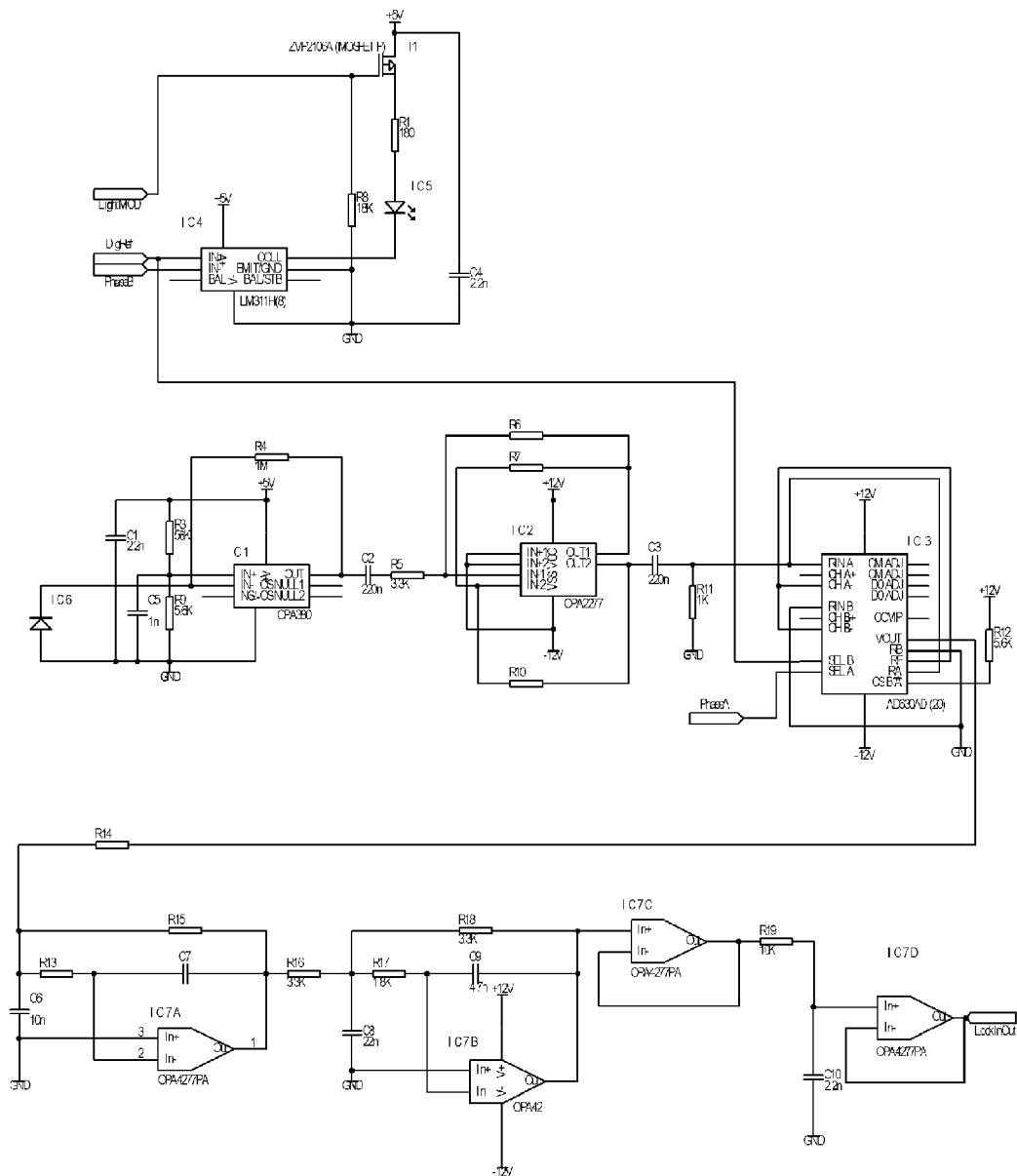
FIG. 7 shows an electronic circuit of the instrument for measurements of the droplet volume.

The detailed diagram of the entire circuit is shown in FIG. 7. The diagram shows the layout for a single channel e.g. fibers 14 and 16, and a pair of one light source and one detector. This includes the LED marked as IC5, the power supply circuit for the LED marked as IC4, the PIN diode marked as IC6, the signal amplifier consisting of the operational amplifiers IC1 and IC2, the phase detector marked as IC3 (AD630). This diagram was used for all the experiments described below. The only difference is that for the experiments with the angle $\Theta=180°$, the amplifier IC2 was bypassed. There was no need for this amplifier as the signal level was sufficiently high for this angle $\Theta$. We also used a different value of the resistance (R1=520Ω) for experiments with $\Theta=180°$ as we could work with lower intensity of the light source under these conditions. Amplifier IC1 is transimpedance amplifier (OPA380). There is high-pass filter installed in between the amplifiers IC1 and IC2 to reject low frequency noise coming from the external light sources (e.g. 100 Hz to 240 Hz). The signal from the output of the phase detector IC3 is filtered by $5^{th}$ order low-pass filter based on IC7A, IC7B, IC7C, IC7D utilizing OPA4277 amplifiers. The frequency modulation unit 22 is not shown in FIG. 7. The modulation frequency used in the experiments described below is in the range of 80-100 kHz and the detection low-pass filter has a corner frequency (3 dB decay frequency) in the range of 2.5-4 kHz. This frequency is adequate for the detection of the droplets dispensed for many applications in the field of the invention. The higher the speed of the droplets, the faster should be the detection circuit. In the experiments described below the signal processing unit was a two channel oscilloscope, e.g. Agilent 54622D two-channel oscilloscope, connected to a PC for data acquisition, storage and analysis. It should be stressed that the circuit presented in FIG. 7 is an example of one embodiment only. Other circuits with similar functionalities could be readily designed by those skilled in the art of circuit design.

The experimental conditions for the angles $\Theta=45°$, $\Theta=90°$ and $\Theta=135°$ were as follows. The frequencies at which the light emitted by the sources 19 and 18 was modulated, were $f_1=107111$ Hz and $f_2=80313$ Hz respectively. The phase shifts between the modulation signal sent to the light source power supply circuit and the reference signal sent to the phase detector $\phi_1$ and $\phi_{0.2}$ were 125° and 123° respectively. The phase shifts and the frequencies were optimized experimentally to increase the signal-to-noise ratio. The positions of the fibers 13, 14, 15 and 16 were adjusted in the body of the housing unit 17 by moving them in and out from the path of the passing droplet. The purpose of the adjustment was to optimize the signal-to-noise ratio of the instrument 9 for the detection of the droplet volume. Typically the adjustment was done for just one liquid, e.g. distilled water and was not altered for other liquids. The length of the fibres 13, 14, 15, 16 was some 0.7 m. We present representative results for signals from the output of the phase-sensitive detectors 25 and 26. As explained above these were measured using a two-channel oscilloscope connected to a PC. The measurements were carried out for droplet volumes of 30 nl, 100 nl, 1000 nl and 10000 nl. 1 nl is one millionth of a milliliter. The volume of the droplet was measured independently and this is described below. The measurements were carried out for several types of liquids. In this specification we include results for the measurements with some of the most common liquids used in assays for life science applications and genomics. These liquids have different optical refraction index and absorption coefficient. The list of testing liquids was carried out as follows:

Liquid 1: Distilled Water, this is the key liquid for many life science applications Liquid 2: Color Dye. 0.5 mg/ml Brilliant Blue FCF in distilled water Maximum absorption of the color dye is located near 640 nm wavelength. As it will be clear from the analysis below, this solution represents the worst case liquid for the conditions when $\Theta$ is substantially different from 180° and the light sources as described above is used (source wavelength is 660 nm). This is precisely the reason why we used it in our experiments. The purpose is to demonstrate operation of the invention under unfavorable conditions. Such a high dye concentration is far beyond the linear range of absorbance vs. concentration curve meaning that in practice it would not be used in real biological assays. On the other hand this should define the best signal when $\Theta$ is substantially equal to 180°.

Liquid 3: 100% undiluted DMSO, the liquid that is commonly used for life science assays and medical diagnostics.

Liquid 4: Buffer PBS 0.01M (Phosphate-buffered saline). This liquid is a representative example of one buffer liquid of a wide range of buffers that are normally used in the field of the invention (e.g. for cell cultures, etc.).

The experimental conditions for the angle $\Theta=180°$ were similar to the ones for other values of the angle with the exception that the frequencies $f_1$ and $f_2$ were 107000 Hz and 77003 Hz respectively. The phase shifts between the modulation signal sent to the light source power supply circuit and the reference signal sent to the phase detector $\phi_1$ and $\phi_{0.2}$ were 15° and 13° for the detectors 20 and 21 respectively.

The experiments described here were performed with the dispenser of the type Equator™ calibrated by means of direct volume measurements for all the four liquids used.

The results of the tests are presented in FIGS. 8 to 20.

Figure 8:
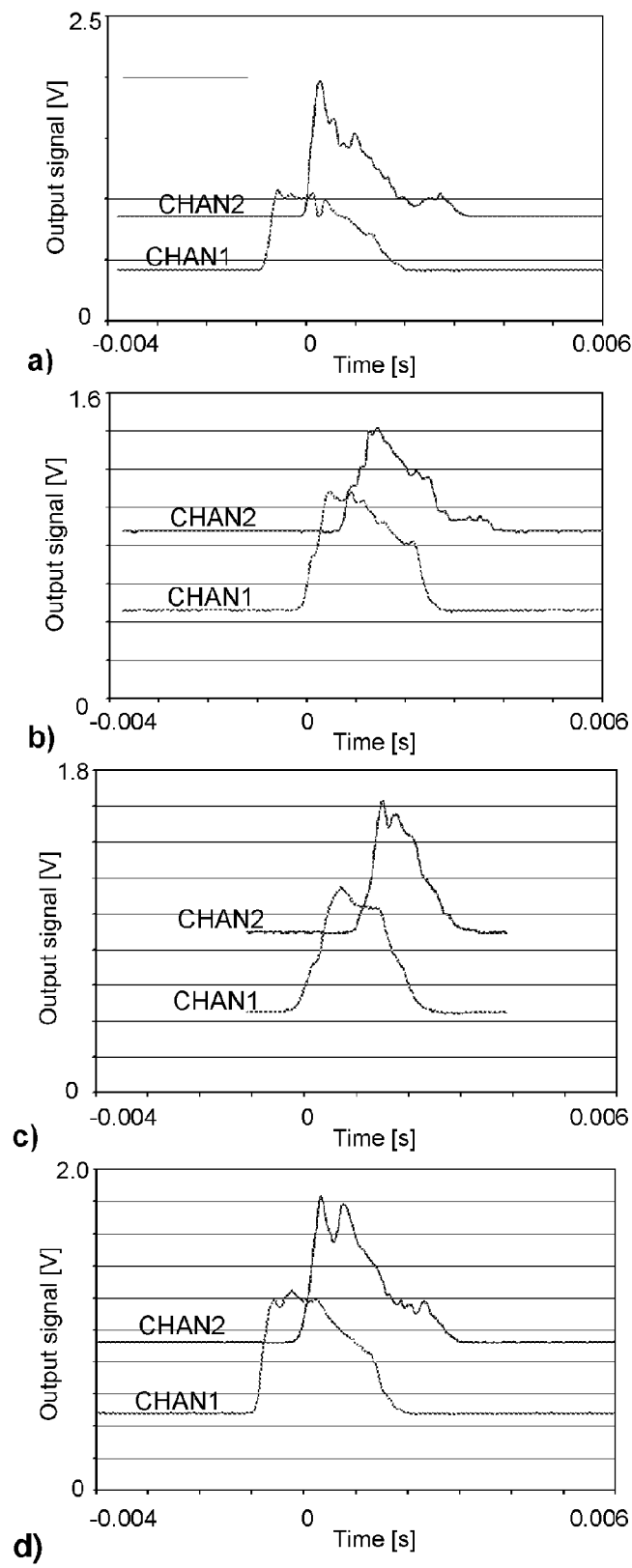
FIGS. 8 to 20 show the output signals from the phase sensitive detectors 25 and 26 for different liquids dispensed, different volumes of the droplets dispensed and different values of the angle Θ.

FIG. 8 shows the output signal from the amplifiers 25 and 26 for $\Theta=45°$ and for droplet volume of 100 nl for the following four liquids: a) distilled water, b) color dye solution, c) 100% DMSO, d) 0.01M PBS.

Figure 9:
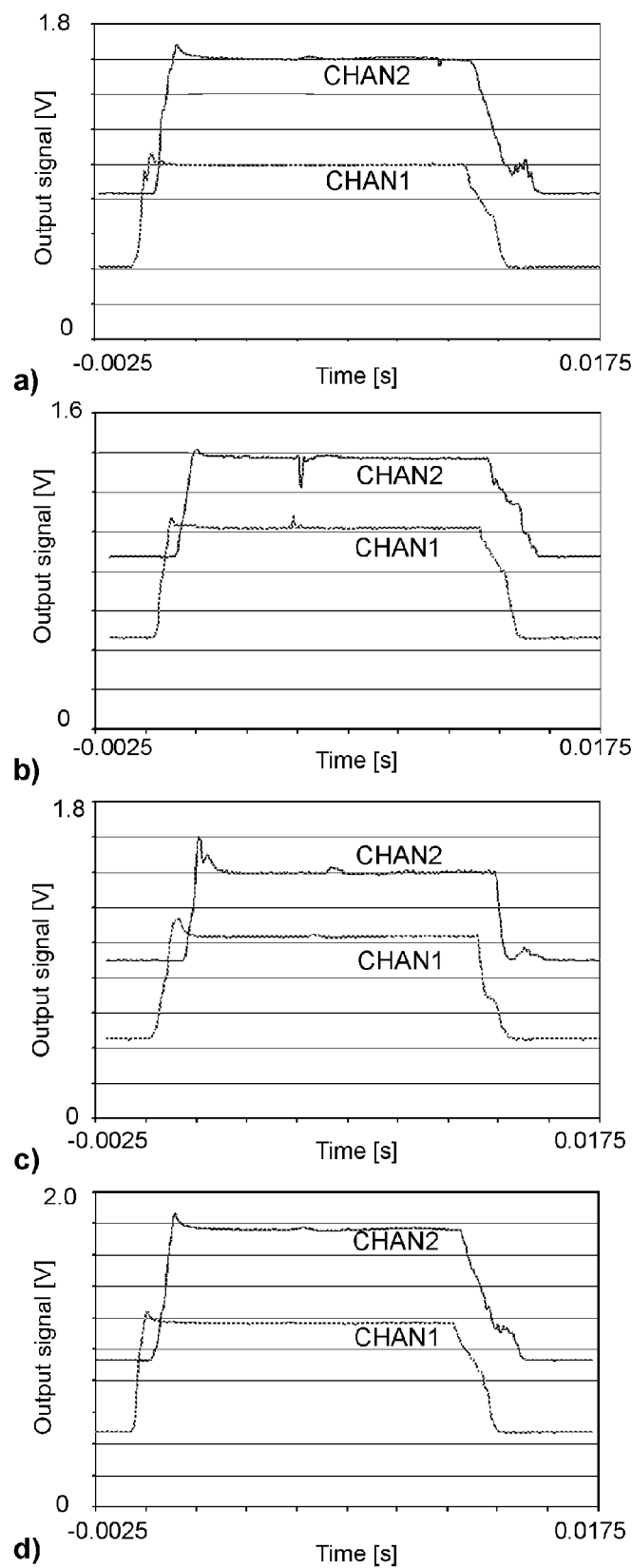

FIG. 9 shows the output signal from the amplifiers 25 and 26 for $\Theta=45°$ and for droplet volume of 1000 nl for the following four liquids: a) distilled water, b) color dye solution, c) 100% DMSO, d) 0.01M PBS.

Figure 10:
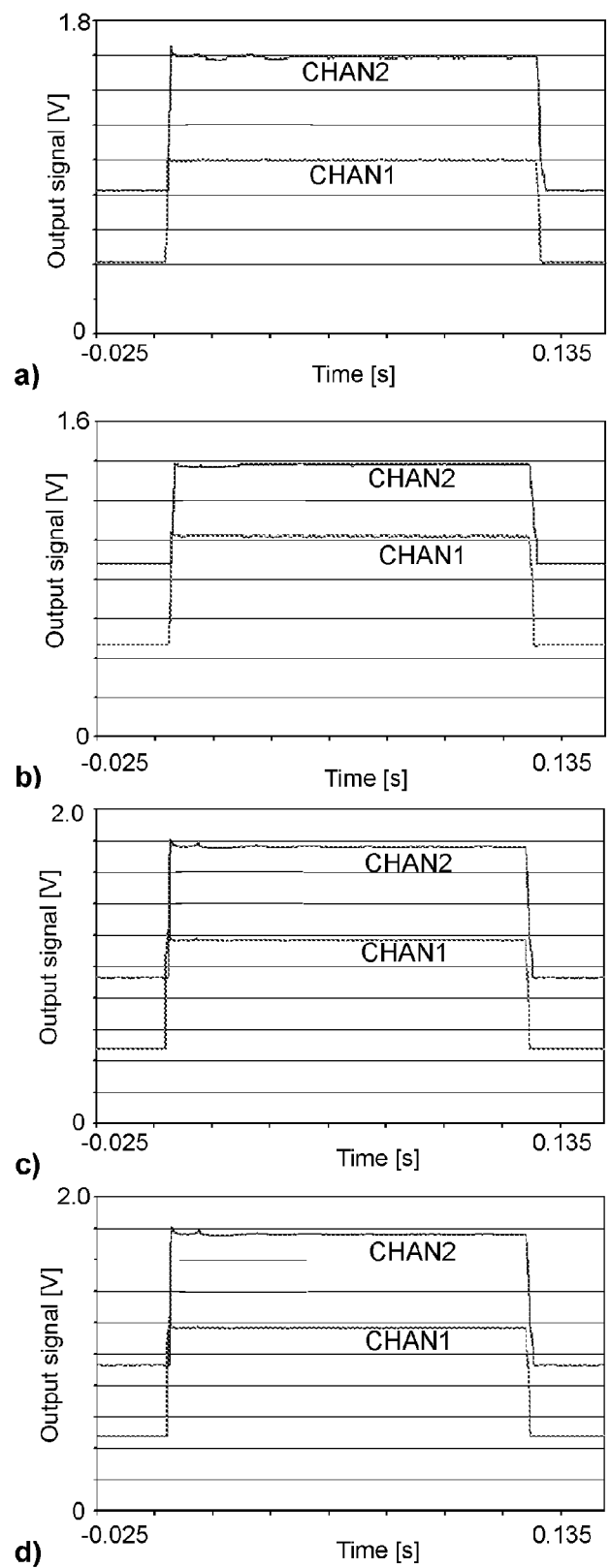

FIG. 10 shows the output signal from the amplifiers 25 and 26 for $\Theta=45°$ and for droplet volume of 10000 nl for the following four liquids: a) distilled water, b) color dye solution, c) 100% DMSO, d) 0.01M PBS.

Figure 11:
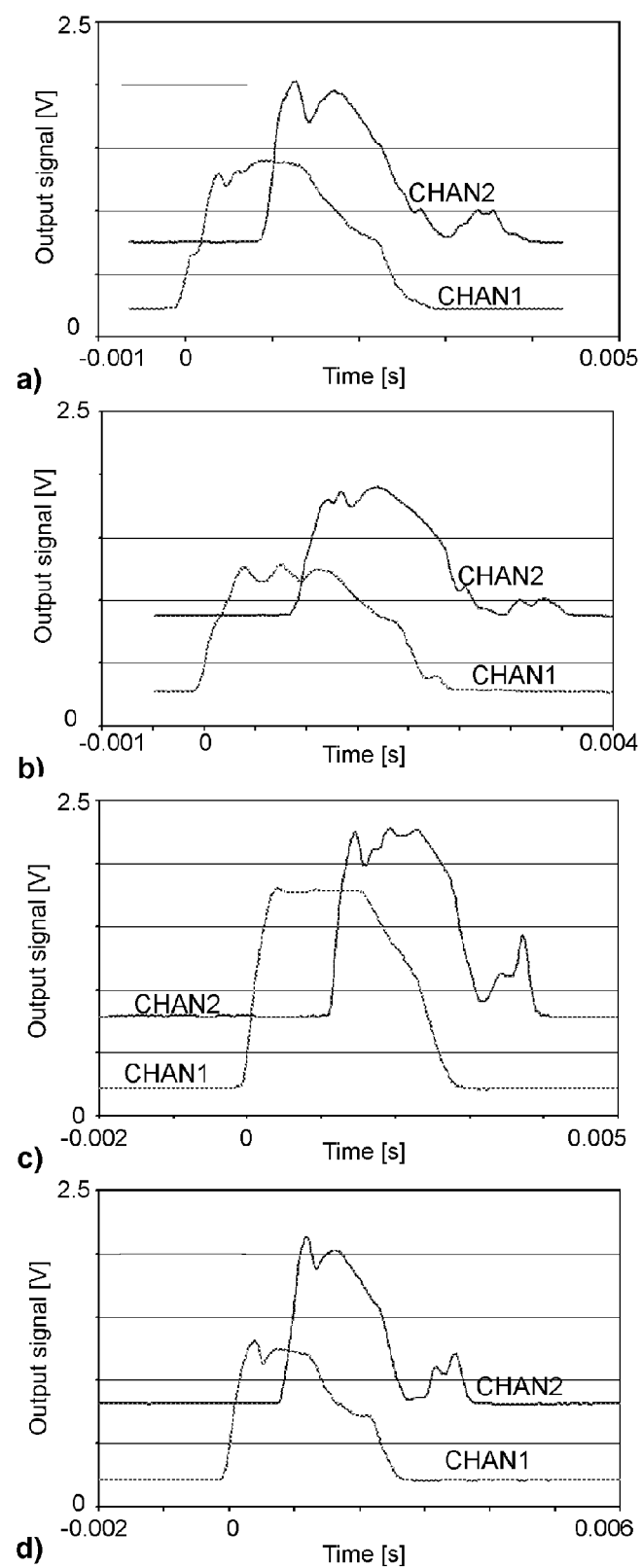

FIG. 11 shows the output signal from the amplifiers 25 and 26 for $\Theta=90°$ and for droplet volume of 100 nl for the following four liquids: a) distilled water, b) color dye solution, c) 100% DMSO, d) 0.01M PBS.

Figure 12:
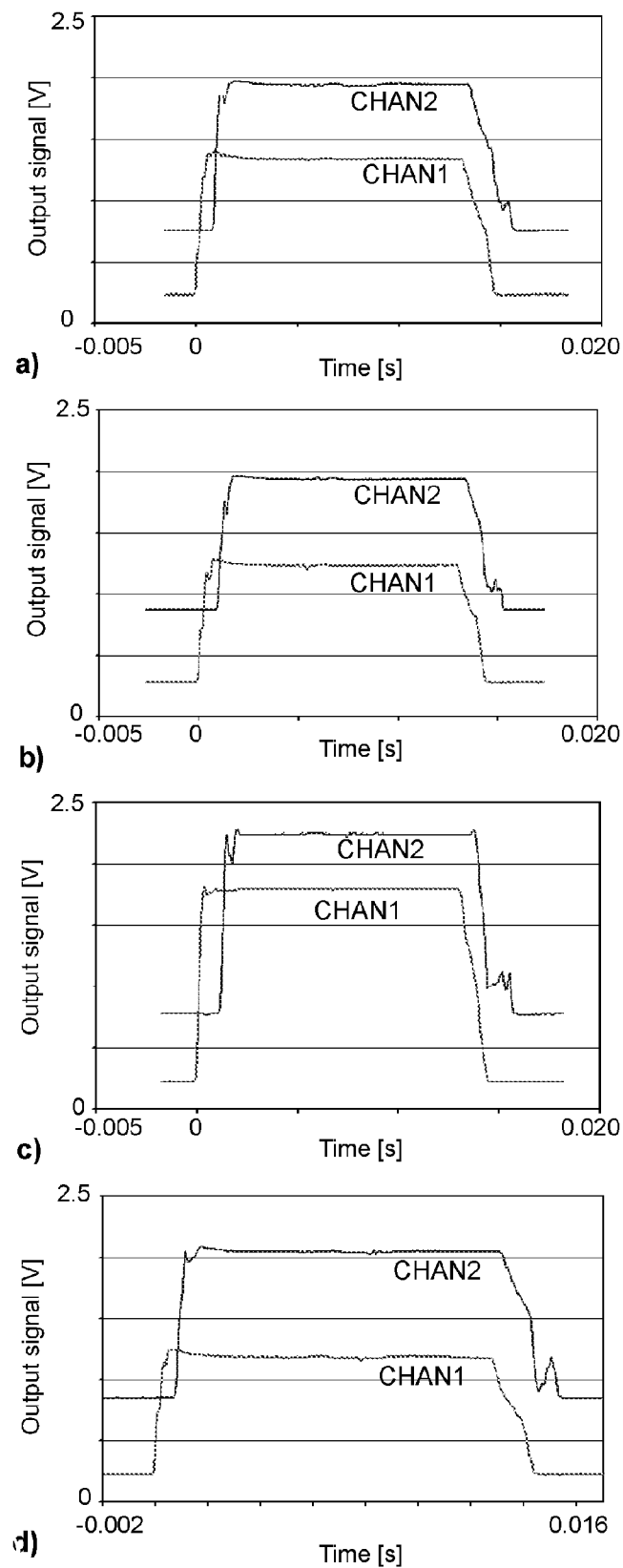

FIG. 12 shows the output signal from the amplifiers 25 and 26 for $\Theta=90°$ and for droplet volume of 1000 nl for the following four liquids: a) distilled water, b) color dye solution, c) 100% DMSO, d) 0.01M PBS.

Figure 13:
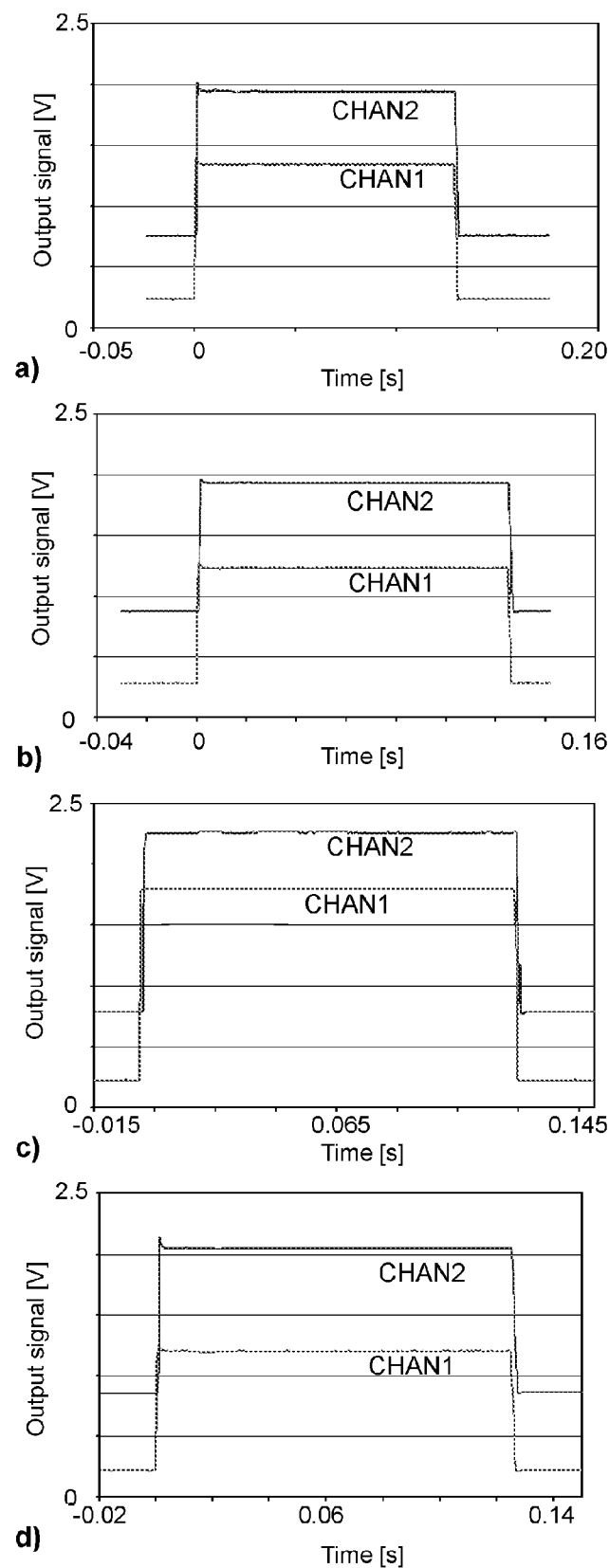

FIG. 13 shows the output signal from the amplifiers 25 and 26 for $\Theta=90°$ and for droplet volume of 10000 nl for the following four liquids: a) distilled water, b) color dye solution, c) 100% DMSO, d) 0.01M PBS.

Figure 14:
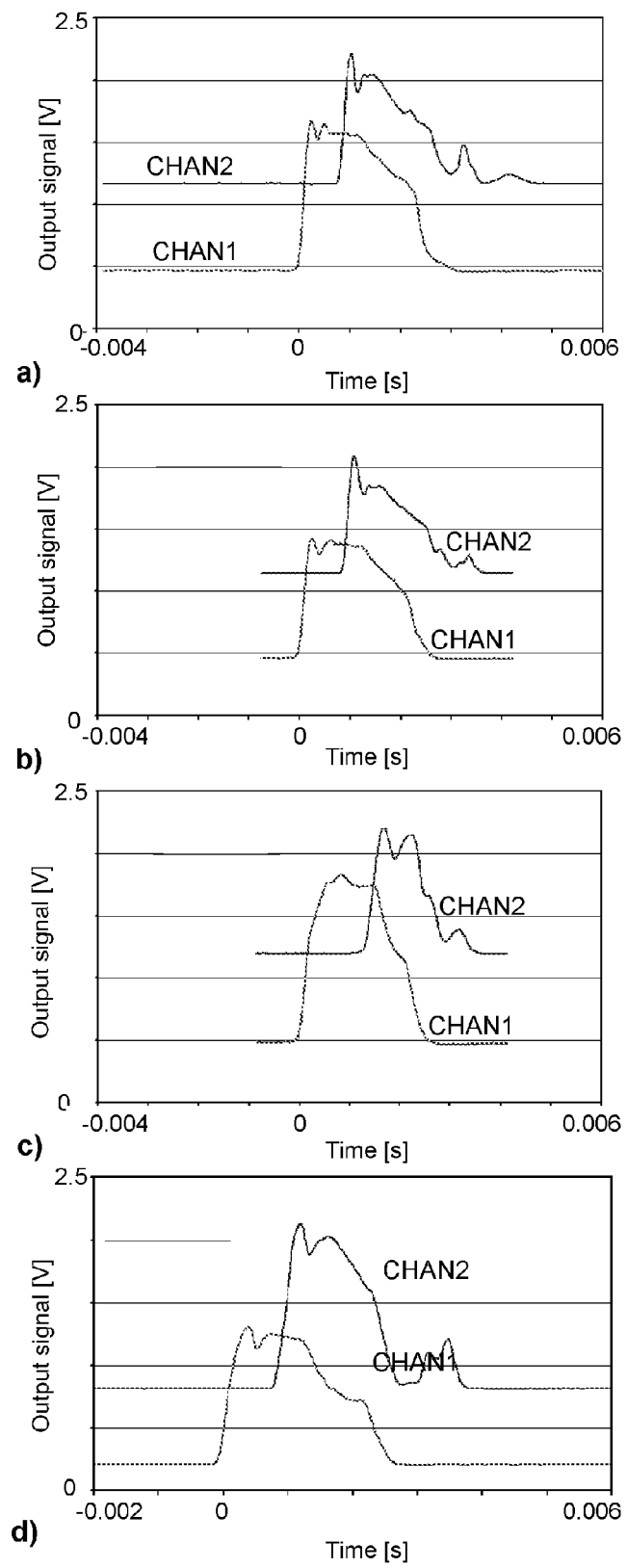

FIG. 14 shows the output signal from the amplifiers 25 and 26 for $\Theta=135°$ and for droplet volume of 100 nl for the following four liquids: a) distilled water, b) color dye solution, c) 100% DMSO, d) 0.01M PBS.

Figure 15:
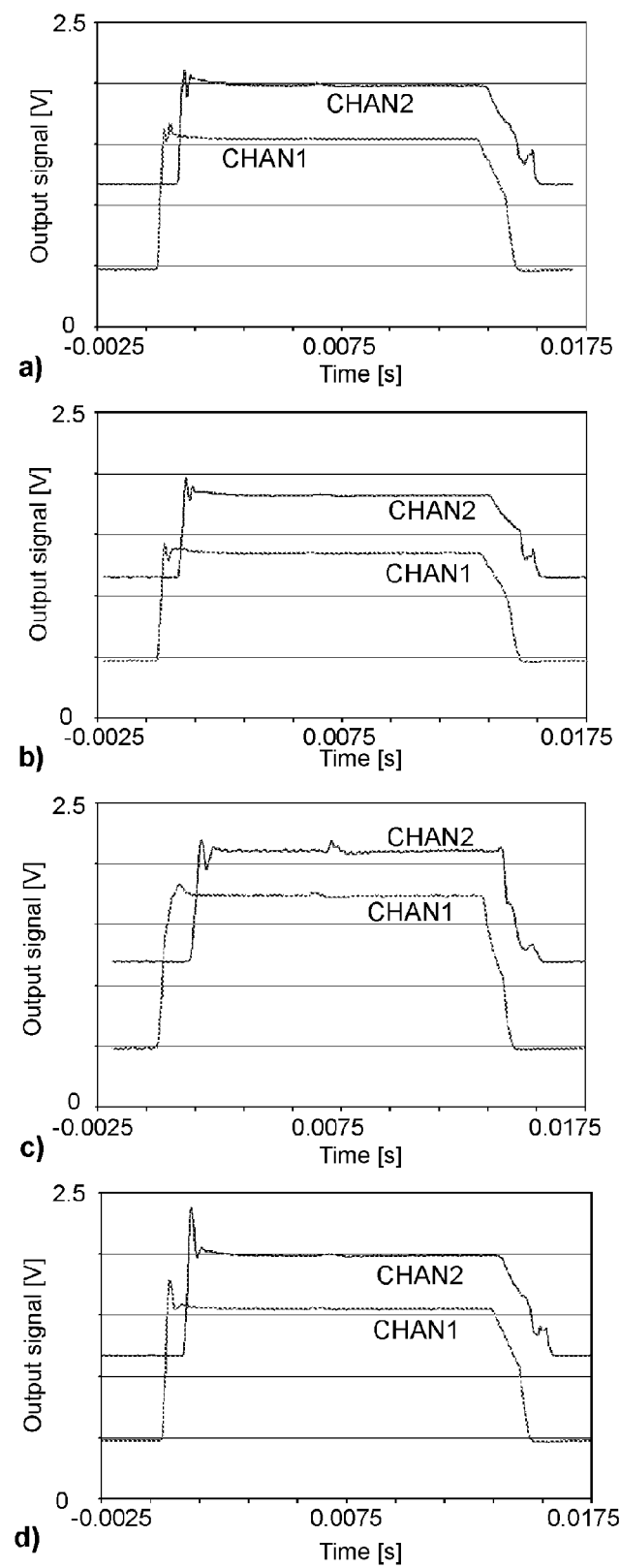

FIG. 15 shows the output signal from the amplifiers 25 and 26 for $\Theta=135°$ and for droplet volume of 1000 nl for the following four liquids: a) distilled water, b) color dye solution, c) 100% DMSO, d) 0.01M PBS.

Figure 16:
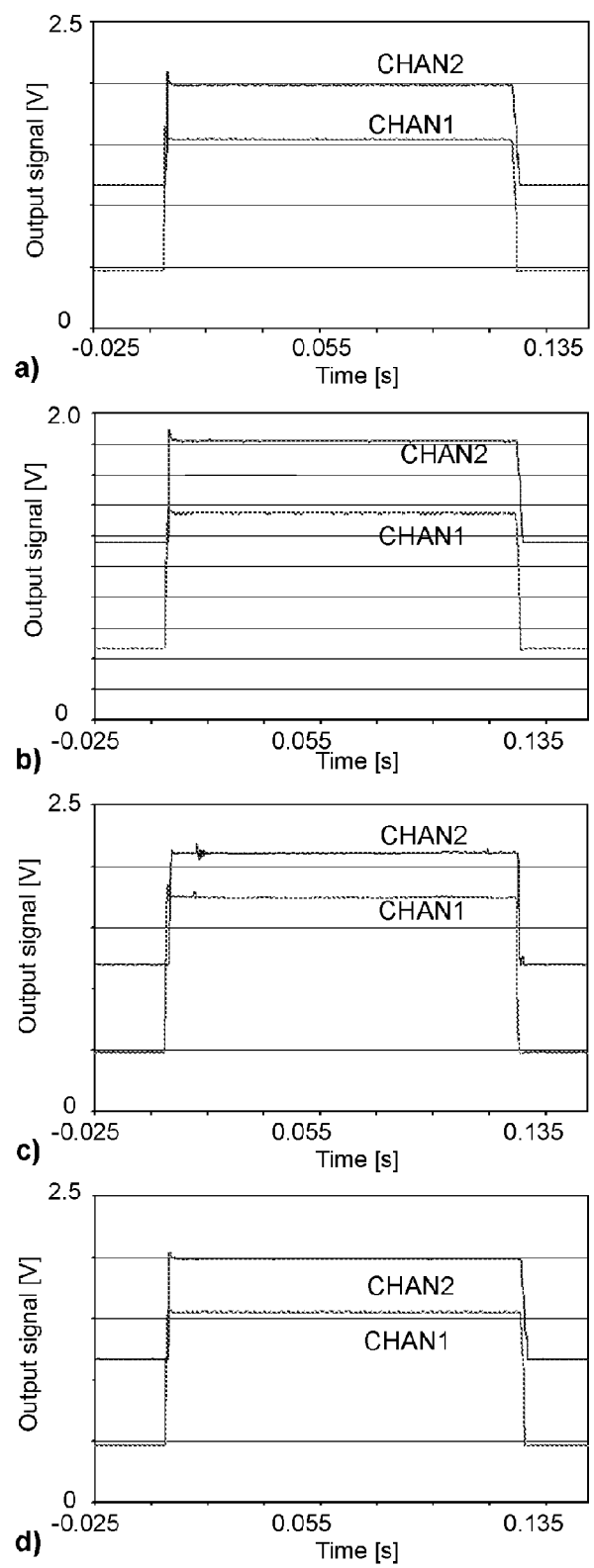

FIG. 16 shows the output signal from the amplifiers 25 and 26 for Θ=135° and for droplet volume of 10000 nl for the following four liquids: a) distilled water, b) color dye solution, c) 100% DMSO, d) 0.01M PBS.

Figure 17:
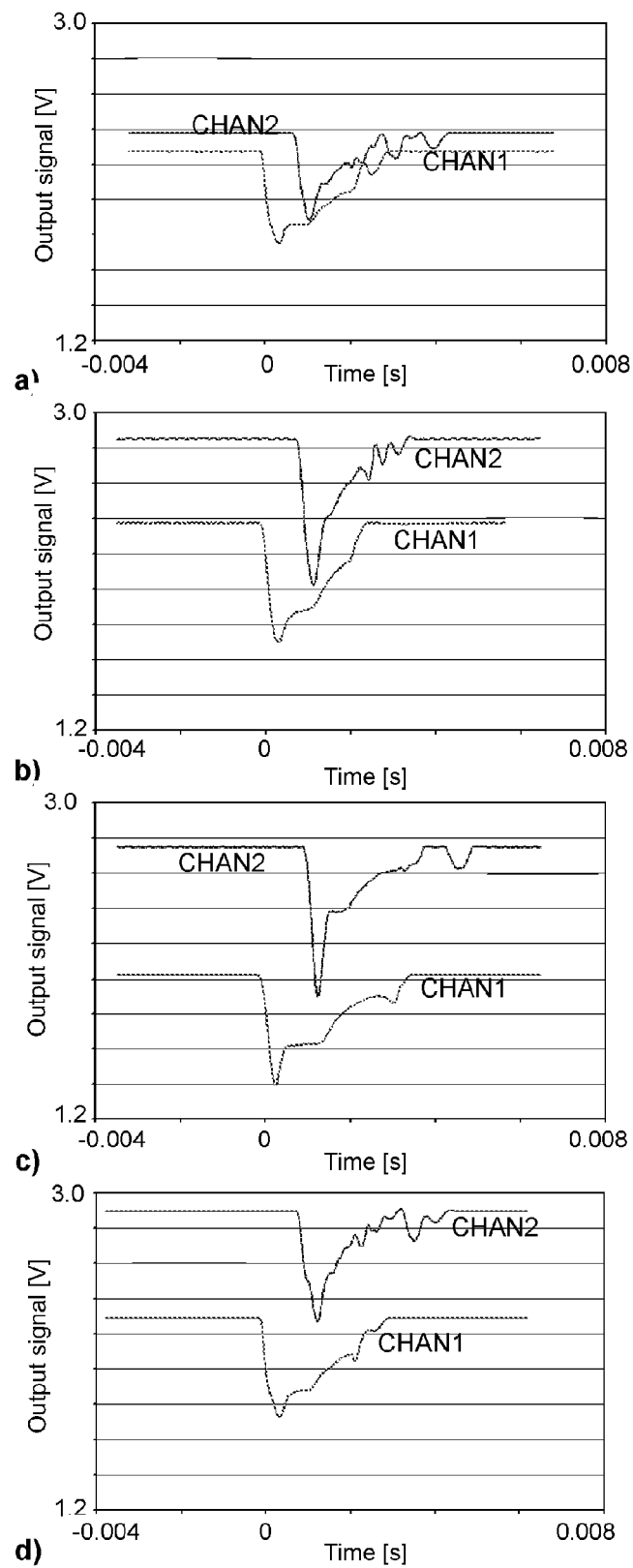

FIG. 17 shows the output signal from the amplifiers 25 and 26 for Θ=180° and for droplet volume of 100 nl for the following four liquids: a) distilled water, b) color dye solution, c) 100% DMSO, d) 0.01M PBS.

Figure 18:
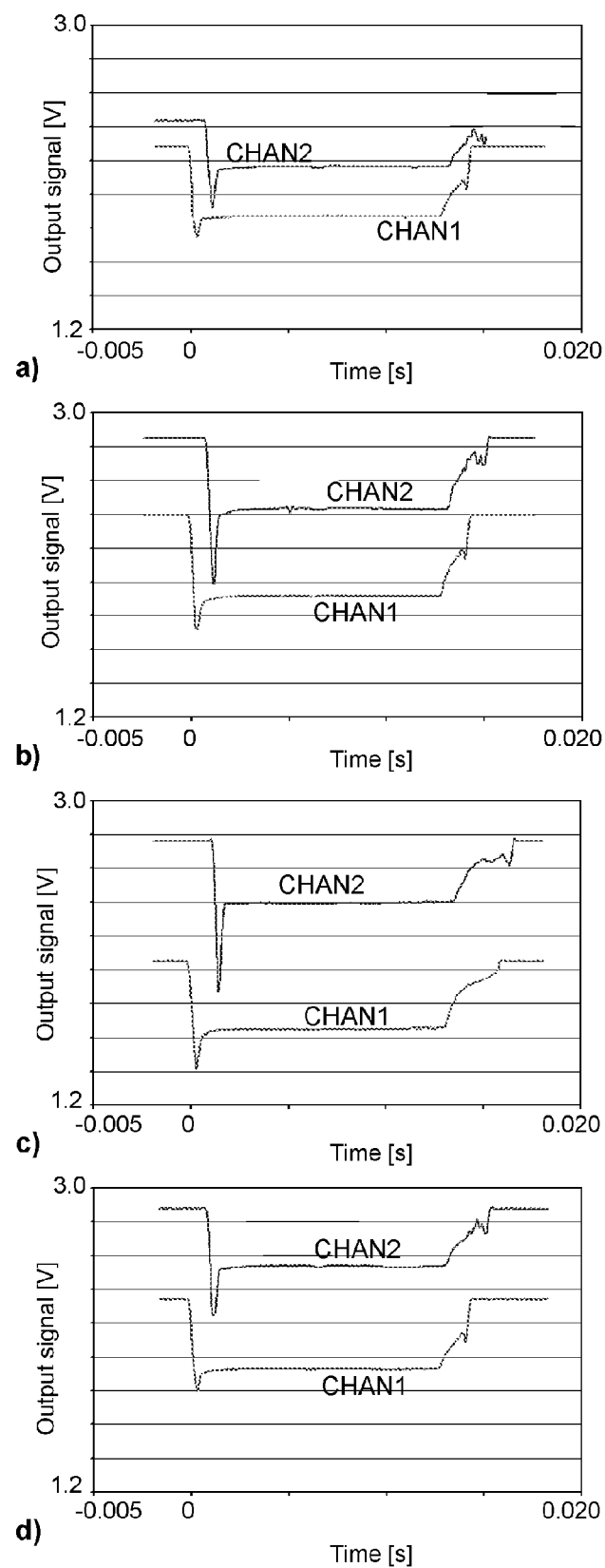

FIG. 18 shows the output signal from the amplifiers 25 and 26 for Θ=180° and for droplet volume of 1000 nl for the following four liquids: a) distilled water, b) color dye solution, c) 100% DMSO, d) 0.01M PBS.

Figure 19:
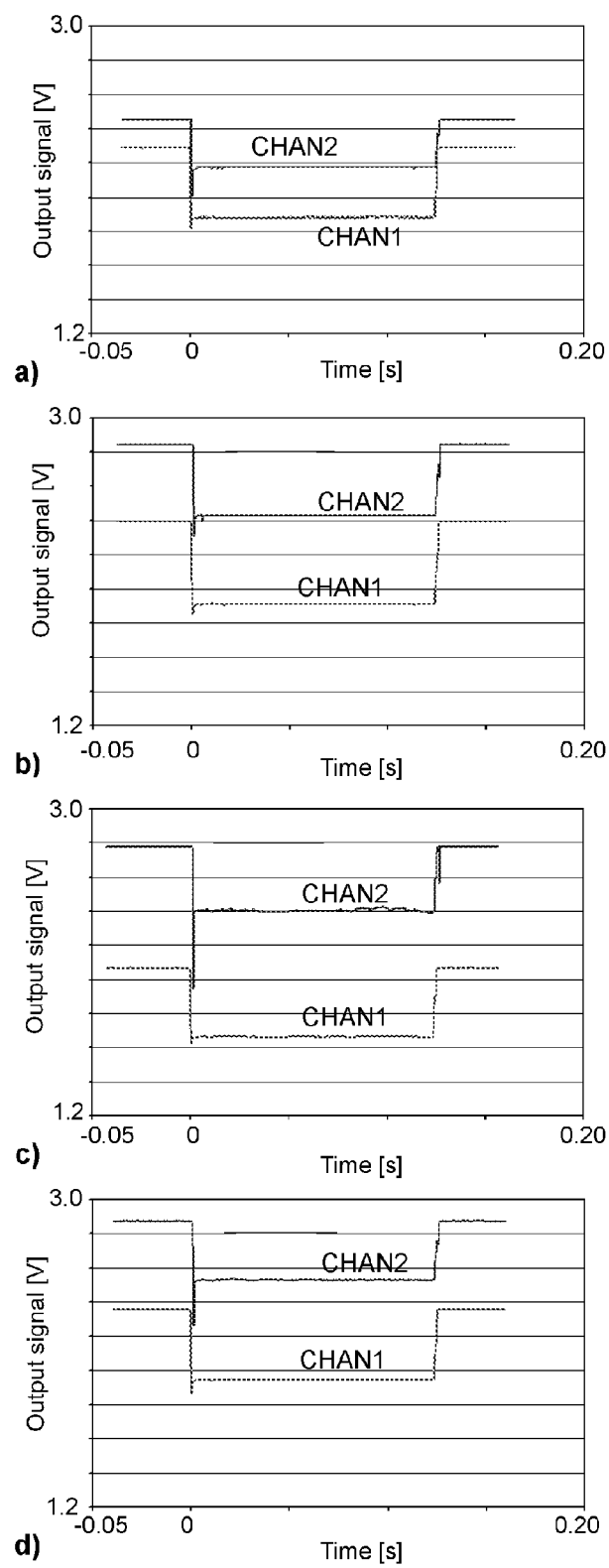

FIG. 19 shows the output signal from the amplifiers 25 and 26 for Θ=180° and for droplet volume of 10000 nl for the following four liquids: a) distilled water, b) color dye solution, c) 100% DMSO, d) 0.01M PBS.

Figure 20:
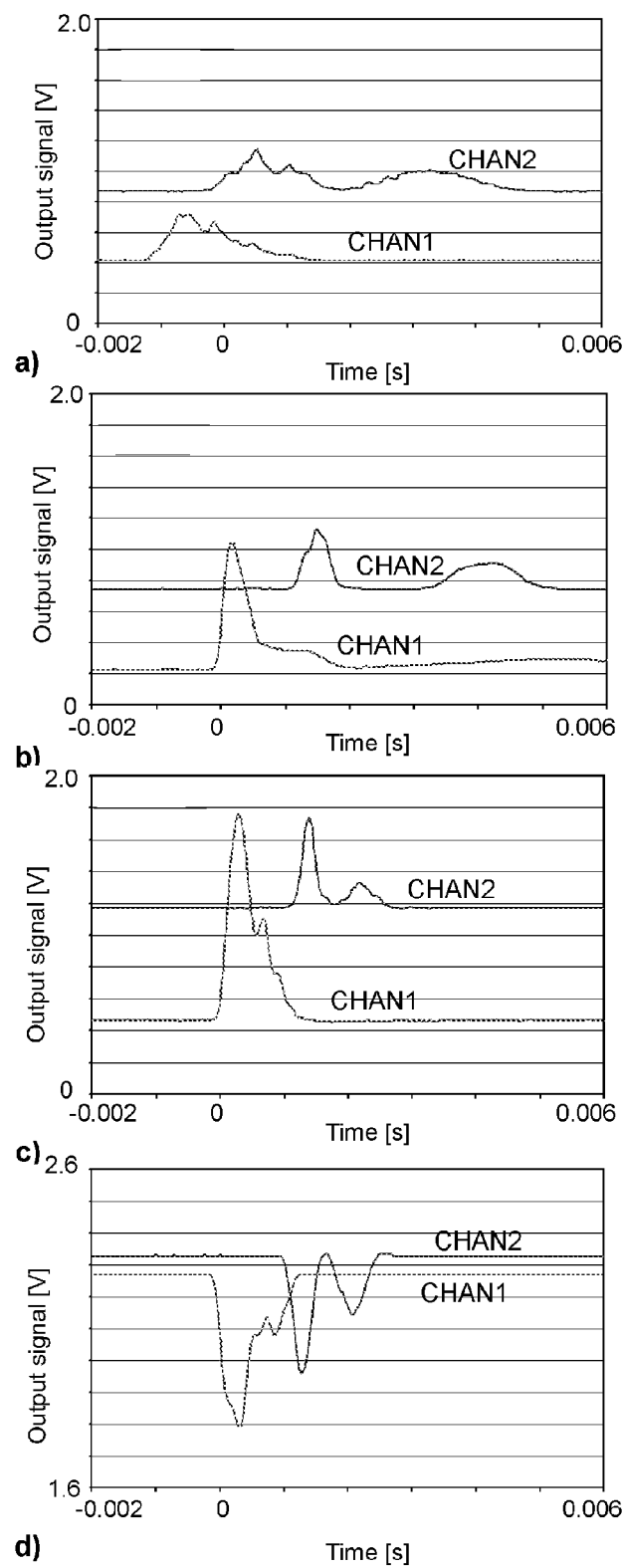

FIG. 20 shows the output signal from the amplifiers 25 and 26 for droplet volume of 30 nl of distilled water for the following four angles Θ a) Θ=45°, b) Θ=90°, c) Θ=135°, d) Θ=180°.

In order to allow comparison of the output signals for different values of the angle Θ and different liquids the following signal factor has been defined:

$$SF = \frac{v_H - v_L}{v_L} \cdot 100\%$$

where $v_L$ is an output signal level (voltage) without a droplet, $v_H$ is an output signal level (voltage) with droplet (saturation value). Saturation value means here not the saturation voltage output of the phase sensitive amplifier but rather voltage output of the amplifier in the middle of the droplet passing in front of the fibers 13, 14, 15, 16. The meaning of the saturation value will be further explained by the discussion related to FIGS. 21, 22. This signal factor is an indication of a ratio between useful (working) signal and background signal. The higher is SF, the better the signal is. The results are presented in Table 1. The second factor given in Table 1, $SF/SF_{water}$, characterizes the ratio of the output signal for a particular testing liquid to the output signal for distilled water (reference liquid).

SF values presented in the Table 1 are calculated as average value for two signals coming from two detection channels.

TABLE 1

Summary of the assessment for the output signal

| Angle Θ | Liquid | SF [%] | $SF/SF_{water}$ [%] |
|---|---|---|---|
| 45° | Distilled Water | 125 | 100 |
| | Color Dye | 78 | 62 |
| | DMSO | 100 | 80 |
| | PBS | 115 | 92 |
| 90° | Distilled Water | 313 | 100 |
| | Color Dye | 99 | 31 |
| | DMSO | 400 | 128 |
| | PBS | 281 | 90 |
| 135° | Distilled Water | 137 | 100 |
| | Color Dye | 110 | 80 |
| | DMSO | 163 | 119 |
| | PBS | 134 | 98 |
| 180° | Distilled Water | 15 | 100 |
| | Color Dye | 24 | 154 |
| | DMSO | 17 | 108 |
| | PBS | 18 | 118 |

The results presented in FIGS. 8 to 20 demonstrate how droplet dispensing can be readily registered by the device of the present invention. Here we describe the method for actual measuring of droplet volume on the basis of these results. As explained above (see in particular FIGS. 1, 2 and related description), the shape of the droplet dispensed evolves as the droplet travels between the nozzle of the dispenser and the destination substrate.

According to the method proposed in this invention, the optical fibers 13, 14, 15, 16 should be located at such a distance from the nozzle tip 1 that when droplet passes through the area sensed by the fibers, in its development it is either represented by the state A-A or by state B-B or it is located in any stage of development from the state A-A to the state B-B. In the state A-A the droplet can be represented essentially as a continuous cylindrical segment. In the state B-B the droplet can be represented by a train of sub-droplets of substantially similar size moving at substantially equal separation along the same path provided that separation between the individual droplets is smaller than size of the sensing area of the optical fibers. For shortness we will refer to the state A-A or state B-B or any intermittent state reflecting the evolution between these two states as the quasi-cylindrical jet or quasi-cylindrical segment. In simple terms the area the fibers can sense corresponds to their optical aperture. It is clear that strictly speaking the droplet does not form an ideal cylindrical segment at any distance from the nozzle 1. The ideal cylinder shape will be always distorted due to the oscillations in the droplet and the effect of the forces of surface tension which lead to the deviation from the ideal cylinder shape. However, the droplet indeed forms at least a distorted cylindrical segment up to some distance away from the nozzle. This can be explained in terms of FIG. 2. The droplet shown in FIG. 2A represents a distorted cylinder and this can be associated with the stage A-A of its development. In contrast the droplet shown in FIG. 2B represents the state B-B according to the definition above. The droplet in FIG. 2B moved further away from the nozzle. For droplets of larger volumes it may happen that the front of the droplet is represented by the state B-B and the end is by the state A-A.

As stated previously, the term "quasi-cylindrical" used in this specification covers liquids dispensed from circular and non-circular nozzles. For example, the nozzle may have an opening of square cross-section, rectangular cross-section, oval cross-section or indeed any other cross-section. A circular cross-section is the most practical one for use in many situations as capillaries of circular cross-section are readily available from numerous manufacturers of capillaries. Furthermore, the circular cross-section is easy to analyze due to its rotational symmetry. However, even if the jet is ejected from a non-circular nozzle, it will evolve to the circular cross-section due to action of surface tension as it travels away from the nozzle. This will normally happen after several oscillations of the cross-sectional shape taking place as the jet travels away from the nozzle. Thus the term "quasi-cylindrical" used herein covers such situations of jets emitted from non-cylindrical nozzles even if the term cylindrical in simple geometry conventions may only be limited to cylinders of circular shape.

Figure 21:
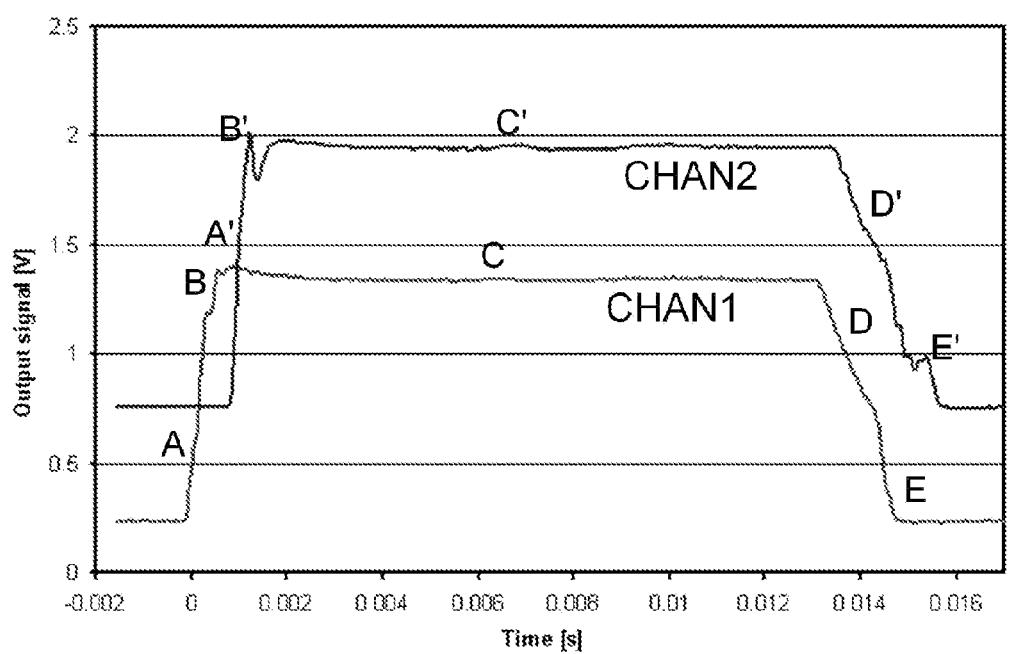
FIG. 21 shows the results of the signal at the output of the phase sensitive detectors 25 and 26.
Figure 22:
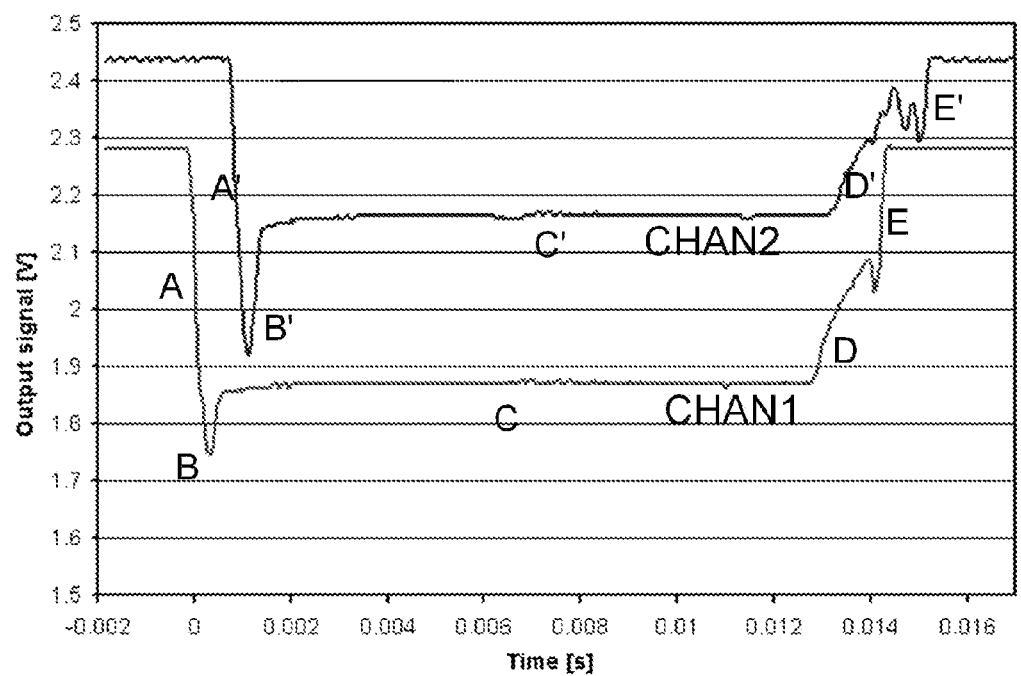
FIG. 22 shows the results of the signal at the output of the phase sensitive detectors 25 and 26.

Formula $t_{breakup} = k(\rho R_o^3/\sigma)^{1/2}$ described above suggests the time required for the droplet to evolve from the state A-A to the state B-B. Therefore, if the distance from the nozzle end 1 to the region sensed by the fibers 13, 14, 15, 16 is smaller than $t_{Breakup} * v_J$, where $v_J$ is the velocity of the droplet, then it arrives to the sensing area substantially in the state A-A. It is difficult to give analytical formula for the time that the droplet remains in the state B-B. This depends on its velocity and radius of the sub-droplets. However, it is easy to see experimentally if the droplet has evolved past the state B-B by the time it has arrived to the sensing area. This is explained in detail further on. The velocity $v_j$ depends on the type of the dispensing instrument used. For example, in the case of the dispensing instrument as described in the U.S. Pat. No. 6,713,021 (Shvets) and U.S. Pat. No. 6,669,909 (Shvets), the velocity is determined by the inner diameter of the nozzle, its length, the pressure in the dispenser and the viscosity of the liquid dispensed. For a typical practical dispenser utilising the concept described in the U.S. Pat. No. 6,713,021 (Shvets) and No. 6,669,909 (Shvets), the velocity is in the range of 0.1 to 20 m/sec. If required, this could be increased up to 200 m/sec or reduced to below 0.01 m/sec using essentially similar type of dispenser simply by changing the pressure in the dispenser, the nozzle diameter and its length. For dispensers of other kinds the velocities of the jet may be outside the range of 0.01 to 200 m/sec. Below four different embodiments of the method that allows measuring the droplet volume from the signals obtained from the phase sensitive detectors 25 and 26 are described. However, before describing the method involved, it is necessary to explain in detail the signal shape and its time dependency at the output of the phase sensitive detectors 25 and 26. This is done with reference to FIGS. 21 and 22. FIG. 21 shows the typical output from the detectors 25 and 26 for the angle $\Theta=45°$. FIG. 22 shows the signal for similar dispensing conditions and the angle $\Theta=180°$.

Once the forehead (3) of a droplet approaches the sensing area, this results in a sharp signal rise in the case of $\Theta=45°$ or a signal drop in case of $\Theta=180°$. This stage is marked by A, A' in FIGS. 21 and 22. Due to the surface tension and air friction the forehead of the jet forms a ball-like shape. This is shown in FIG. 1B. The presence of the ball-like forehead results in a slight peak in the signal following the stage marked by letters A, A' and described above. This peak is positive for $\Theta=450$ and negative for $\Theta=180°$. For the data presented in FIGS. 21 and 22, the peak is more profound for $\Theta=180°$ as the liquid ball at the jet forehead absorbs more light than the jet segment that follows it. The stage representing the passing of the ball-like forehead through the sensing area of the fibers 13, 14, 15, 16 is marked by letters B, B' in FIGS. 21 and 22. Once the jet is fully positioned in the sensing area of the fibers, i.e. spreads through the entire aperture of the fibers 13, 14, 15, 16, the signal is saturated. This stage is marked by letters C, C' in FIGS. 21 and 22. Once the valve or another mechanism controlling the dispensing is closed, the supply of liquid to the nozzle discontinues and the jet narrows down as shown in FIG. 1D. This results in a signal drop. By comparison to the signal rising slope, the rate of this signal drop is usually relatively slow. This stage is marked by letters D, D' in FIGS. 21 and 22. Finally, the jet breaks away from the nozzle. This is seen in the signal stage marked by letters E, E' in FIGS. 21 and 22. The process of separation of the jet from the nozzle often has somewhat random character and often minute droplets are formed at the location where the jet is separated from the nozzle 1. Sometimes, these tiny droplets may return back to the nozzle, i.e. they may travel in the direction opposite to the jet. In some cases they follow the main jet as separate droplets and in some cases they travel faster than the main jet and therefore, catch up with the jet tail. These processes can be seen from spurious signal, small signal peaks, etc as marked by letters E, E' in FIGS. 21 and 22.

Figure 23:
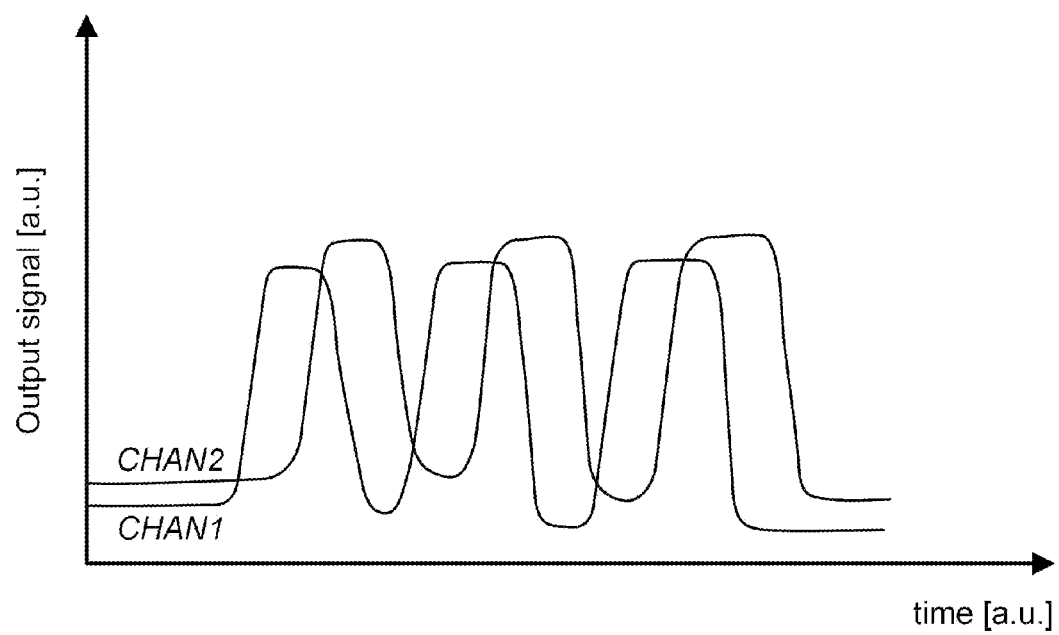
FIG. 23 shows the result of the signal at the output of the phase sensitive detectors 25 and 26 in the situation where the droplet is not in state B-B and does not form the continuous jet segment.
Figure 24:
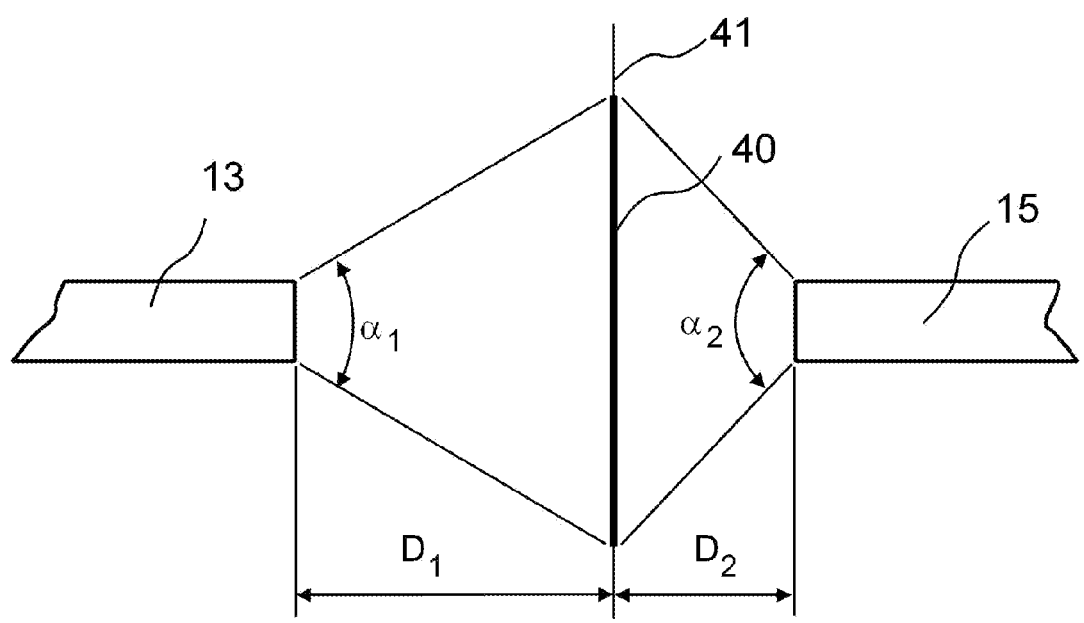
FIG. 24 shows schematics of the sensitive area of the fibers 13 and 15.

It should be stressed that if the droplet is not in the state A-A, i.e. it does not form the continuous jet but is rather in the state B-B when passing in front of the optical fibers 13, 14, 15, 16, it can still leave the output trace similar to the one shown in FIGS. 21, 22. This will be true provided that several sub-droplets appear simultaneously in the sensing area of the two optical fibers coupled to each other, e.g. fibers 13 and 15. If sub-droplets pass the sensing area one-by-one and the time constant of the amplifiers 25 and 26 is sufficiently short to detect passing of the individual droplets, then the dependency of the signal will be as shown in FIG. 23. This figure shows the segment of jet separated into three separate sub-droplets passing in front of the optical fiber. In this case the sensing area of the fiber is reduced to capture just a single droplet at a time. The size of the sensing area of the fibers depends of the numerical aperture of the fibers and the separation between their ends. This is schematically shown in FIG. 24. The size of the sensing area can be increased if the separation between the ends of the fibers is increased or if the fibers with greater numerical aperture are used. This will be clear to those skilled in fiber optics. The numerical aperture of the fibers 13 and 15 is indicated schematically by letters $\alpha_1$ and $\alpha_2$. The size of the sensing area is indicated by the numeral 40. Line 41 indicates the trajectory of the passing jet. The separations from the ends of the fibers 13 and 15 to the line 41 are indicated by the letters $D_1$ and $D_2$.

Four embodiments of the method for measurement of the droplet volume are described below. These embodiments are described in relation to the droplet in the state A-A. Further we also make reference to the droplet in the state B-B and indicate that under certain conditions the same method can applied to such droplets.

Figure 25:
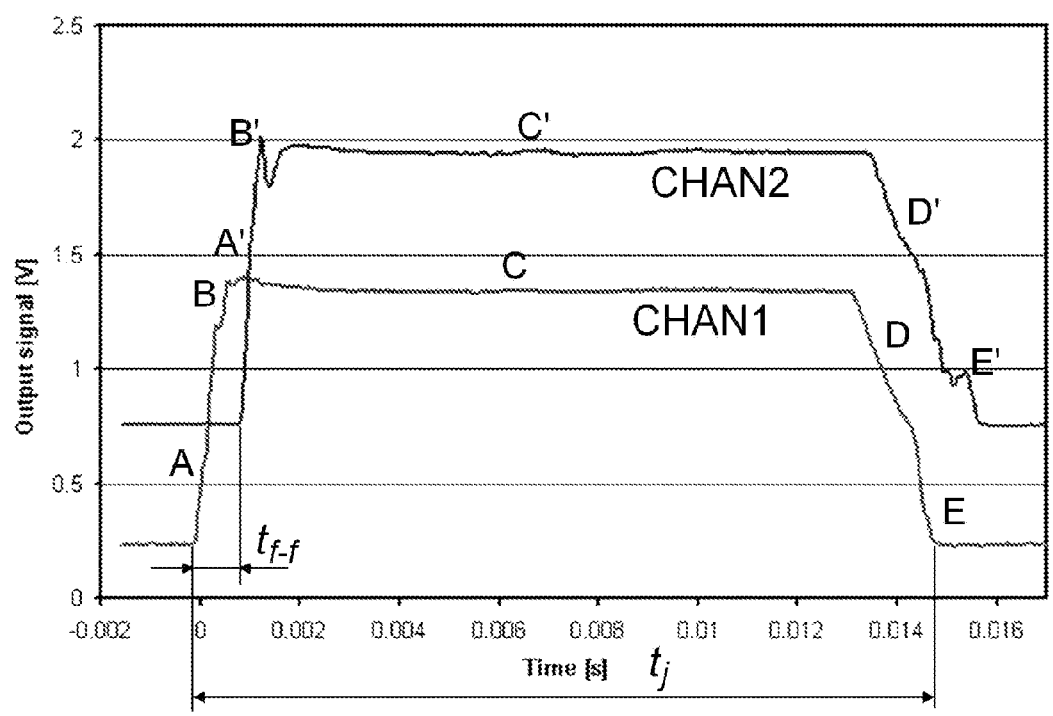
FIG. 25 shows the results of the signal output of the phase sensitive detectors 25 and 26 in relation to the method for measuring the droplet described.

The first embodiment of the method is based on measurement of the jet length $l_j$. It is explained with reference to FIG. 25. At a relatively short distance away from the nozzle the jet in the typical volume range of interest to the field of the invention can be represented as a cylindrical segment. The diameter of the jet $2R_0$ (twice the radius) is typically essentially equivalent to the inner diameter $(2r)$ (twice the radius) of the nozzle and it is uniform throughout the length of the jet segment. We shall explain later what defines the difference between the diameter of the jet $2R_0$ and the inner diameter of the nozzle $2r$. Then the cross-sectional area of the jet is $\pi R_0^2$. Therefore the volume of the jet is substantially equal to $V_j = l_j \pi R_0^2$. The length of the jet segment $l_j$ can be measured from the signal at the output of the phase sensitive detectors 25 and 26: $l_j = v_j t_j$. Here $t_j$ is the time required for the jet segment to pass in front of the optical fiber, e.g. fiber 14 or fiber 13 and $v_j$ is the velocity of the jet. The velocity of the jet can be calculated from the time delay $t_{f-f}$ between the fronts A and A' and the separation $l_{f-f}$ between sensing areas of the optical fibers 13 and 14. For example, if the separation between the fibers is $l_{f-f}=2$ mm and the time $t_{f-f}$ is $10^{-3}$ sec, then the velocity $v_j = l_{f-f}/t_{f-f} = 2$ m/sec. The values of $t_{f-f}$ and $t_j$ are schematically indicated in FIG. 25. It is therefore one of the findings of the present invention that the velocity of the jet forehead can fairly represent velocity of the entire jet. To measure the values of $t_{f-f}$ and $t_j$ one could e.g. differentiate the signal from the phase sensitive detector. The differentiated signal peaks up at the rising and also the falling front. This allows to determine accurately the timing of the rising and the falling front and therefore the values of $t_{f-f}$ and $t_j$. We shall not expand on this issue any further as it will be known to those skilled in the art of electronics.

Figure 26:
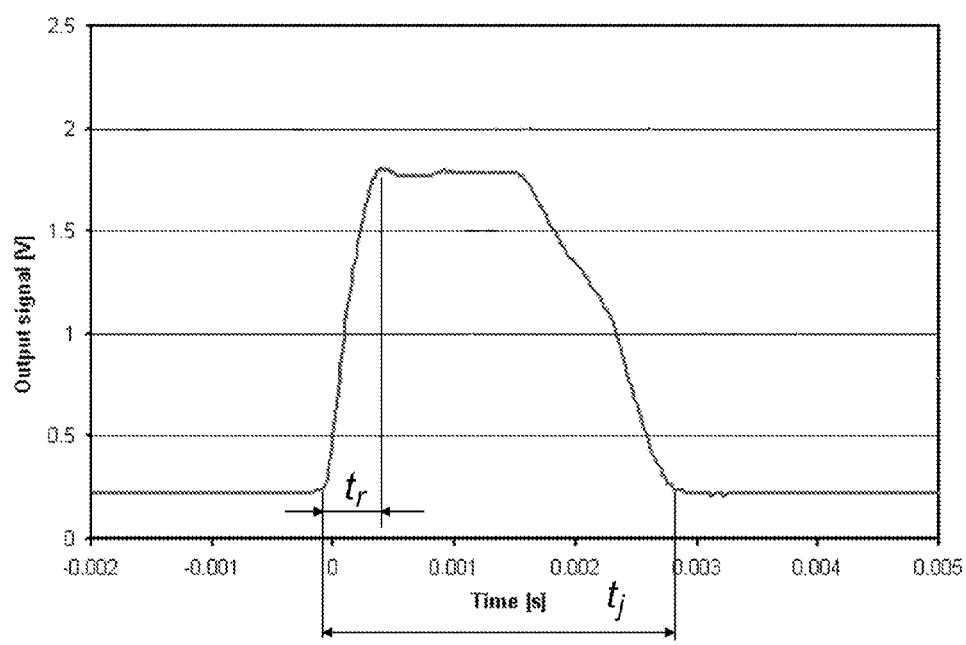
FIG. 26 shows the results of the signal of the phase-sensitive detector 26 in relation to the method for measuring the droplet described.

The second embodiment of the method is explained with reference to FIG. 26. The measurement is based on the signal from the output of a single phase sensitive detector 26. The signal from the second phase sensitive detector 25 is not required for this embodiment. Therefore this embodiment is based on just one set of fibers, e.g. 15 and 13 (or equally, fibers 14 and 16), one light source and one light detector. The jet velocity is measured using a signal slope. For example if the sensing area of the fiber 15 $l_s$ is 1 mm and the time of the signal rise $t_r$ is $30 \times 10^{-5}$ sec, then the jet velocity is $v_j = l_s/t_r = 3.3$ m/sec. The jet length $l_j$ is determined as above using the value of the time $t_j$. The values of $t_r$ and $t_j$ are schematically indicated in FIG. 26. Again we do not discuss the methods for the extraction of the values of $t_r$ and $t_j$ from the signal profile. The extraction could be achieved by means of analogue circuits, e.g. integrating and differentiating circuits or by means of conversion of the signal into digital form and then processing it. These will be well known to those skilled in the art.

It should be stressed that the droplet may split into a train of sub-droplets (quasi-cylindrical) and it can still produce a signal when passing in front of the optical fibers 13, 14, 15, 16 at the phase sensitive detectors 25, 26 as if it were a continuous jet segment. This is provided that a number of such sub-droplets appear in the sensing area of the fibers simultaneously. This observation forms one of the key aspects and unexpected findings of the present invention. Such a state of the droplet is called in the invention state B-B. In fact in the experiments presented in FIGS. 8-22, the droplet passes the sensing area of the first set of fibers 16 and 14 as a continuous jet, i.e. in the state A-A and the sensing area of the second set of fibers 15 and 13 the jet passes in the state B-B. We have established this experimentally using a high speed camera where the evolution of the droplet was studied at different distances away from the nozzle. This observation is also broadly consistent with the formula $$t_{breakup} = k(\rho R_o^3/\sigma)^{1/2}$$

which gives the distance traveled by the droplet in the state A-A as $l_{A-A} = t_{breakup} v_j$, $v_j$ being the droplet velocity. The formula gives the values of $l_{A-A}$ in the range of 2-5 mm meaning that the transition from the state A-A into the state B-B happens around the second set of fibers 13 and 15. The invention demonstrates that such a transition does not affect the signal too much although the accuracy of measurements is somewhat compromised. This is well illustrated by data presented in FIGS. 8-22. The signal from the Channel 2 (phase sensitive detector 26) generally mimics rather closely the signal from the Channel 1 (phase sensitive detector 25). However, the signal of the Channel 2 is noisier and for some dispensing volumes it may contain spurious peaks. In our experiment the size of the sensing area of the fibers is some 2 mm in diameter. Generally for the droplets ejected from the nozzle of 150 micron internal diameter there are some 3-4 droplets appearing in the sensing area at any given moment during the dispensing. This is because the separation between the sub-droplets in this case is some only 0.6-0.8 mm.

Figure 27:
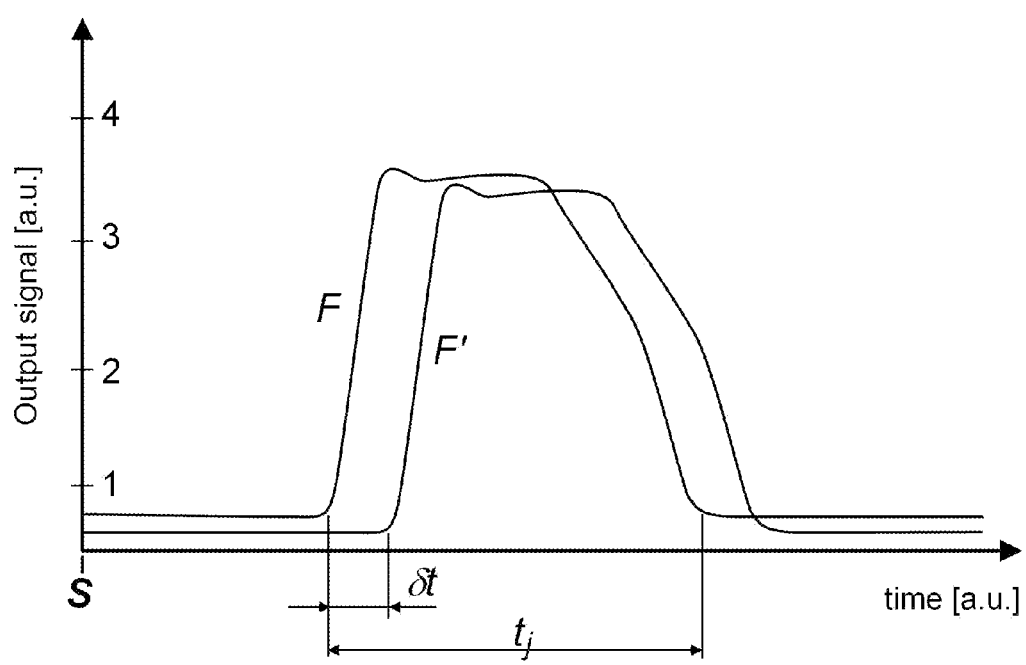
FIG. 27 shows two subsequent recorded signals of a single phase sensitive detector for two positions of the nozzle.

The third embodiment of the method is also based on the signal from the output of a single phase sensitive detector, e.g. detector 26. In this method velocity of the jet is measured by means of the time delay $t_d$ between the start of the dispensing and the moment when the jet's forehead is detected by the detector 26. The velocity $v_j$ is then measured as $v_j = l_d/l_t$ where $l_d$ is the distance between the end of the nozzle 1 and the upper part of the sensing area of the fiber, i.e. that part of the sensing area that is closer to the end of the nozzle 1. The length $l_j$ of the jet is defined from the value of time $t_j$ as in the second embodiment. If the distance $l_d$ is not known, then the embodiment could be altered as follows as explained with reference to FIG. 27. The signal from the phase-sensitive detector is measured for a given position of the nozzle. This is represented by the curve F in FIG. 25. Then the nozzle is displaced essentially along the direction of the jet trajectory by a certain distance $\delta D$. The identical jet is then dispensed again and the signal is recorded for the second time. This is represented by the curve F'. The two curves are essentially identical curves and one of them being merely displaced along the x-axis of the graph in FIG. 27. FIG. 27 shows the case when the nozzle was displaced away from the fiber for the second dispensing indicated by the curve F'. Letter S in FIG. 27 indicates the start of the dispensing. For clarity of the sketch we also displaced the two curves along the y-axis. The scales along the two axes are in arbitrary units. The time interval between the two signals $\delta 6t$ is then extracted from the curves. The jet velocity is calculated as $v_j = \delta D/\delta t$. The length of the jet is calculated as described above using the value of $t_j$ and the jet velocity $v_j$. The disadvantage of this embodiment is that dispensing of two jets is required to determine the droplet volume. Therefore, strictly speaking this approach can not be used for real-time measurements of the droplet volume.

The final embodiment of the method is related to very small droplets that can not be fairly represented by cylindrical segment of a jet. In contrast such droplet can be represented by the sphere-like shape. In this case the signal is not saturated as shown in FIG. 20 and the droplet volume can be estimated according to the following formula:

$$vol = K_s \cdot \int s(t) dt,$$

where $s(t)$ is an output signal (normalized and conditioned in a suitable way), Ks is scaling factor. Typically this embodiment is suitable for very small droplets with the volume below 100 nl but clearly the volume depends on the diameter of the nozzle. The scaling factor Ks can be determined from the calibration of the device using a separate volume measurements device, e.g. micro balance.

Figure 28:
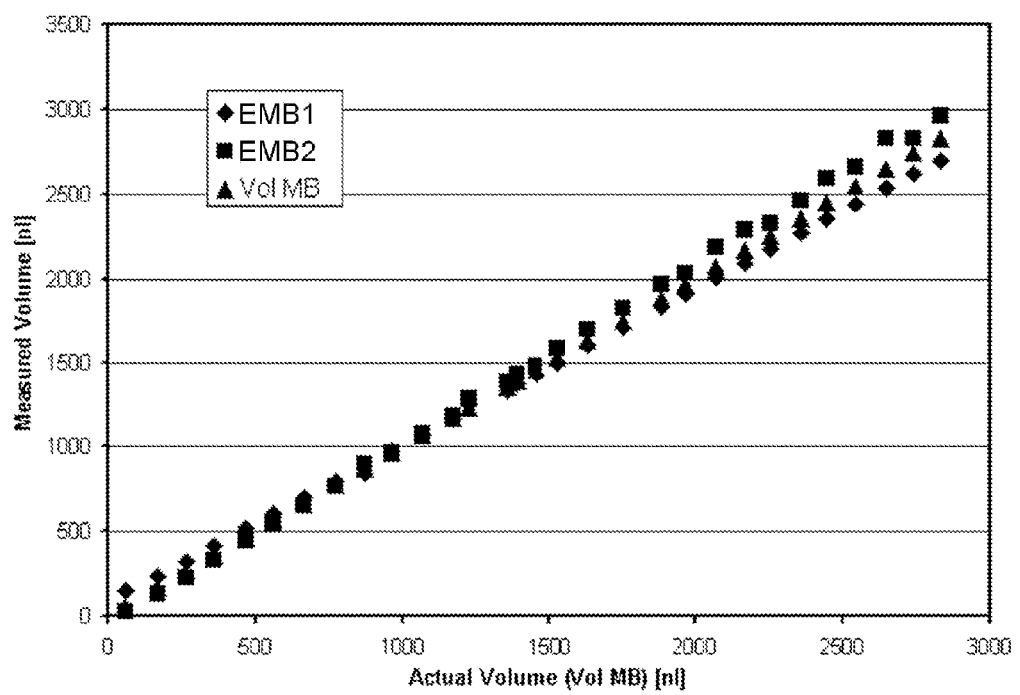
FIG. 28 shows the results for two embodiments of the method for the droplet measurements (EMB1 and EMB2) and also the results of the gravimetric volume measurements presented for comparison and marked by triangles (Vol MB). The liquid dispensed is distilled water and the dispensing pressure is 1400 mBar.
Figure 29:
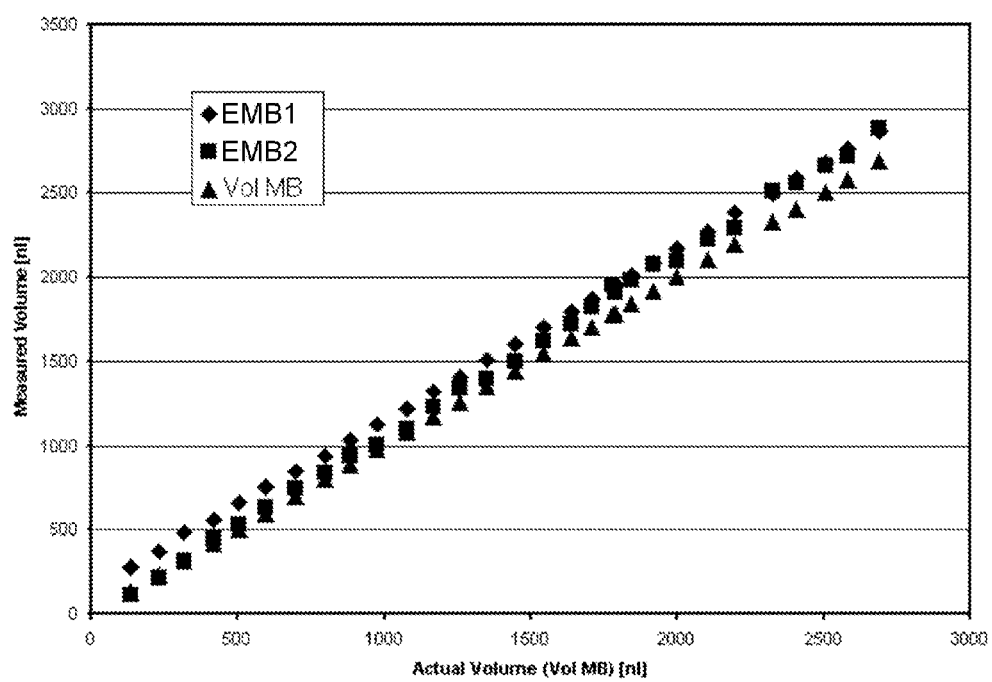
FIG. 29 shows the results for two embodiments of the method for the droplet measurements (EMB1 and EMB2) and also the results of the gravimetric volume measurements presented for comparison and marked by triangles (Vol MB). The liquid dispensed is distilled water and the dispensing pressure is 2000 mBar.

Here we present experimental results on comparison of the accuracy of the first and second embodiments described above. These are marked by the symbols EMB1 and EMB2. For comparison we also presented results of direct volume measurements using microbalance. The latter is marked by the symbol Vol MB. For these experiments we developed dedicated software. The software integrates and controls Spot-on™ dispenser, Agilent oscilloscope used for data acquisition and storage, and Sartorius MC5 microbalance. The experimental setup allows simultaneous dispensation and measurement of the volume of each separate droplet by volume measurements device according to the first and second embodiments. It also measures the volume dispensed using the gravimetric method and microbalance. Representative results obtained are given in FIGS. 28 and 29. The tests have been performed for distilled water dispensed by two different dispensing pressures. The droplet velocity is proportional to the dispensing pressure. FIG. 28 represents the ejection at the pressure of 1400 mBar and FIG. 29 represents ejection at the pressure 2000 mBar. Each point in the chart represents an average of three consecutive measurements for the certain requested volume.

Table 2. Average error for two tested embodiments for volume range: 300 nl-3000 nl.

|  | Average error for the range 300 nl-3000 nl [%] Distilled water @ 1400 mBar | Average error for the range 300 nl-3000 nl [%] Distilled water @ 2000 mBar |
| --- | --- | --- |
| Embodiment 1 | 0.41 | 14.47 |
| Embodiment 2 | 1.92 | −6.96 |

It will be understood that the invention does not need to be used with the nozzles of cylindrical shape. If the nozzle is not of cylindrical shape, then in the formulas for the droplet volume we need to substitute the cross-sectional area of the nozzle instead of the value $\pi r^2$.

Furthermore, it should be noted that the diameter of the jet in the state A-A is not necessarily equal to the inner diameter of the nozzle even though the two values are usually rather close. In the results presented in FIGS. 28 and 29 the diameter of the jet was calculated to be 0.180 mm whereas the internal diameter of the nozzle was 0.152 mm. Our experiments suggest that the diameter of the jet is in between the values of the inner and outer diameters of the nozzle. The greater is the jet velocity; the closer is the diameter of the jet to the inner diameter of the nozzle. The difference between the inner diameter and the jet diameter also depends on the surface tension a of the liquid dispensed. Therefore in general when using the embodiments 1, 2, 3 of the method for the droplet measurements described above, it is beneficial to evaluate the diameter of the jet on the basis of the direct volume calibration.

Figure 30:
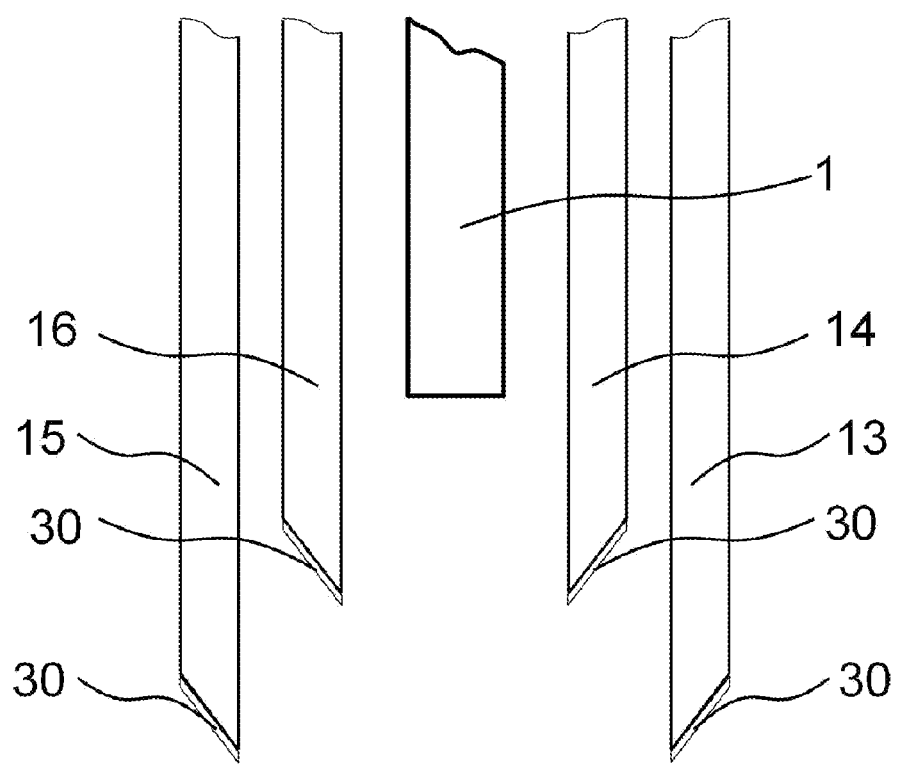
FIG. 30 shows element of another possible embodiment of the device 9.
Figure 31:
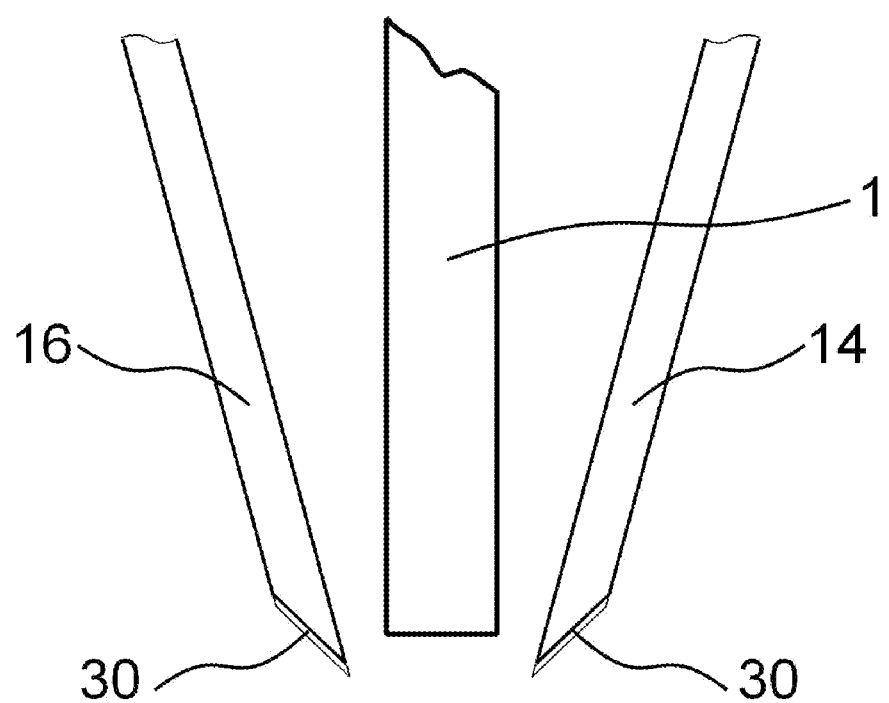
FIG. 31 shows element of another possible embodiment of the device 9.

FIG. 30 shows element of another possible embodiment of the device 9. It shows the positions of the optical fibers 13, 14, 15 and 16. All the other elements of the device are similar to the ones described with reference to FIG. 4. In this case the ends of the fibers 13, 14, 15, 16 are aligned substantially along the pathway of the jet. The FIG. 30 shows the embodiment then they are actually aligned parallel to the pathway of the jet. It should be appreciated that the fibers could also form angle with the pathway of the jet as shown in FIG. 31. The ends of the fibers are cut in such a way that they form surface tilted with respect to its axis. The end of the fiber is treated so that it forms a preferably reflective surface marked by numeral 30. Methods of achieving reflective surface at the end of the fiber are well known to those skilled in the art and therefore will not be discussed here in further detail. FIG. 30 shows embodiment when the fibers 13 and 14 are positioned on one side of the nozzle 1 and the fibers 15, 16 are directly on the opposite side. This is done only for the simplicity of the figure. One could readily design embodiments where the axes of the fibers e.g. 13, 15 and the axis of the nozzle (the pathway of the jet) are not in the same plane. Furthermore, the all the fibers 13, 14, 15, 16 do not need to be positioned the same distance away from the nozzle. This is done merely for simplicity of the FIGS. 30 and 31. The light from the fiber 15 is coupled into the fiber 13 via the jet meaning that the amount of light coupled is altered when the jet is passing in the vicinity of the ends of the fibers. The same applies to the fibers 16 and 14: the light from the fiber 16 is coupled into the fiber 14 via the jet. The presence of the reflective surfaces at the ends of the fibers 13, 14, 15, 16 increases the efficiency of the coupling. The operation of this embodiment is similar to the one described with reference to FIG. 3.

Those skilled in the art of electronics measurements equipment will readily appreciate that the phase-sensitive detectors do not have to be used. One could readily device the embodiment of the device with other types of amplifiers.

It should be further stressed that the wavelength of light coupled into the fibers 15 and 16 could be different. This increases the complexity of the system but reduces the crosstalk between the pairs of fibers so that the signal coupled into the fiber 14 from the fiber 15 as well as the signal coupled into the fiber 13 from the fiber 15 is minimized. Those skilled in the art of fiber optics will appreciate that for this the filters need to be used. For example, if the light coupled into the fibers 15 and 16 is at the wavelengths $\lambda_1$ and $\lambda_2$ then band-pass filters could be installed at the output of the fibers 13 and 14 that transmit the light at the wavelengths $\lambda_1$ and $\lambda_2$ respectively. This ensures for example that the light from the fiber 15 is coupled into the fiber 13 but not into the fiber 14.

It should be noticed that embodiment of the device could be constructed in which detection of the droplet takes place simultaneously for several angles $\Theta$. This increases complexity of the instrument but in some cases may lead to improved accuracy and robustness of the droplet measurements. For example, embodiment could be constructed having two fibers 14' and 14" coupled to the fiber 16. The angle $\Theta$ between the fibers 16 and 14' could be 180° and the angle $\Theta$ between the fibers 16 and 14" could be 90°. Clearly, other values of the angles could be chosen. In this case two sets of amplifiers and filters may need to be used. This could be marked with numerals 21', 21", 23', 23", 25', 25".

In the specification, the terms "comprise, comprises, comprised and comprising" or any variation thereof and the term "include, includes, included and including" or any variation thereof are considered to be totally interchangeable and they should be afforded the widest possible interpretation.

It will be understood that the present invention is not limited to the objects and embodiments described herein but may be varied both in construction and detail within the scope of the claims.

We claim:

1. A liquid droplet monitoring and measuring apparatus for measuring a volume of a dispensed liquid as it is being discharged from a liquid dispensing system with a liquid dispensing tip, the apparatus comprising:
   an optical sensing unit located at a distance from the liquid dispensing tip and configured to measure a change in optical signal output as the liquid is dispensed and further configured to sense a cylindrical or quasi-cylindrical liquid jet dispensed from the liquid dispensing tip; and
   a signal processing unit coupled to the optical sensing unit and configured to process information associated with the change in optical signal output, determine a length for the dispensed cylindrical or quasi-cylindrical liquid jet based on at least information associated with the change in optical signal output, and determine a volume of the dispensed cylindrical or quasi-cylindrical liquid jet based on at least information associated with the determined length.

2. The apparatus as recited in claim 1 wherein the signal processing unit is further configured to determine the volume of the dispensed cylindrical or quasi-cylindrical liquid jet ranging from approximately 1 nl to approximately 1000 µl.

3. The apparatus as recited in claim 1 wherein the optical sensing unit comprises an optical housing unit including a body for accommodating one or more optical fibers; and the one or more optical fibers are connectable with one or more optical source units and one or more optical detector units, such that the optical housing unit is configured to be mounted adjacent to the dispensing tip.

4. The apparatus as recited in claim 3 wherein the optical housing unit comprises:
   an optical housing body;
   at least two optical fibers located adjacent to the liquid dispensing tip;
   at least one optical source unit coupled to the at least two optical fibers; and
   at least one optical detector unit.

5. The apparatus as recited in claim 3 wherein the optical housing unit comprises one or more pairs of optical fibers.

6. The apparatus as recited in claim 3 wherein the optical housing unit comprises one pair of optical fibers, one optical source unit and one optical detector unit.

7. The apparatus as recited in claim 3 wherein the optical housing unit comprises a pair of optical fibers, one of which is connected to a light source and the other one connected to a detector, and in which an angle between the pair of optical fibers ranging from 45° to 180°.

8. The apparatus as recited in claim 3 wherein the one or more optical fibers are releasably or permanently fixed to the body.

9. The apparatus as recited in claim 3 wherein open ends of the one or more optical fibers are oriented substantially parallel to a path of the dispensed liquid jet.

10. The apparatus as recited in claim 3 wherein the one or more optical fibers are oriented at an angle with a path of the dispensed liquid jet.

11. The apparatus as recited in claim 3 wherein a distance from the one or more optical fibers to a path of the dispensed liquid jet ranges from approximately 0.1 mm to approximately 20 mm.

12. The apparatus as recited in claim 3 wherein a distance between each of the one or more optical fibers and a path of the dispensed liquid jet is different.

13. The apparatus as recited in claim 3 wherein the one or more optical source units comprise a light-emitting diode or a diode laser.

14. The apparatus as recited in claim 3 wherein the one or more optical detector units comprise a phase sensitive detector.

15. The apparatus of claim 1 is a part of a dispensing assembly for liquid droplets of the order of approximately 1000 µl or less in volume comprising also a nozzle including the liquid dispensing tip for delivering the liquid through the nozzle onto a receiving substrate.

* * * * *